US005639866A

United States Patent [19]
Kahne

[11] Patent Number: 5,639,866
[45] Date of Patent: Jun. 17, 1997

[54] SINGLE-STEP FORMATION OF MULTIPLE GLYCOSIDIC LINKAGES

[75] Inventor: Daniel Evan Kahne, Princeton, N.J.

[73] Assignee: Princeton University, Princeton, N.J.

[21] Appl. No.: 21,391

[22] Filed: Feb. 23, 1993

[51] Int. Cl.$^6$ .............................. C07G 3/00; C07H 15/00
[52] U.S. Cl. .................... 536/18.6; 536/1.11; 536/4.1; 536/18.5; 536/124; 536/126
[58] Field of Search ........................... 536/1.11, 4.1, 536/18.5, 18.6, 124, 126

[56] References Cited

U.S. PATENT DOCUMENTS

| | | |
|---|---|---|
| 4,046,886 | 9/1977 | Smith . |
| 4,130,643 | 12/1978 | Smith . |
| 4,130,667 | 12/1978 | Smith . |
| 4,148,887 | 4/1979 | Smith . |
| 4,148,893 | 4/1979 | Smith . |
| 4,148,917 | 4/1979 | Smith . |
| 4,148,924 | 4/1979 | Smith et al. . |
| 4,470,976 | 9/1984 | Miner et al. . |
| 4,548,922 | 10/1985 | Carey et al. . |
| 4,746,508 | 5/1988 | Carey et al. . |
| 4,865,848 | 9/1989 | Cheng et al. . |
| 4,902,505 | 2/1990 | Pardridge et al. . |
| 5,338,837 | 8/1994 | Kahne ........................................ 536/5 |

FOREIGN PATENT DOCUMENTS

| | | |
|---|---|---|
| 0 285 285 | 10/1988 | European Pat. Off. . |
| 0 444 778 A1 | 9/1991 | European Pat. Off. . |
| WO90/03172 | 4/1990 | WIPO . |
| WO90/13298 | 11/1990 | WIPO . |
| WO9311772 | 6/1993 | WIPO . |

OTHER PUBLICATIONS

Ito et al "Tetrahedron Letters" (1987) vol. 28 #40, 4701–4.
Kahne et al J. Am. Chem. Soc. (1989) 111 pp. 6881–6882.
Ito et al. "Tetrahed Lts" (1988) vol. 29 #9 pp. 1061–1064.
Feizi et al. *TIBS*, 1985, 24.
Rademacher et al. *Annu. Rev. Biochem.* 1988, 57, 785.
Feizi *TIBS*, 1991, 84.
Dennis and Laferte *Cancer Res.* 1985, 45, 6034.
Fishman *J. Membr. Biol.* 1982, 69, 85.
Markwell et al. *PNAS USA*, 1981, 78, 5406.
Wiley and Skehel *J. Annu. Rev. Biochem.* 1987, 56, 365.
Kleinman et al. *PNAS USA*, 1979, 76, 3367.
Walz et al. *Science* 1990, 250.
Furka et al. *Int. J. Peptide Protein Res.* 1991, 37, 487.
Lam et al. *Nature* 1991, 354, 82.
Houghten *Nature* 1991, 354, 84.
Zuckermann et al. *Proc. Natl. Acad. Sci. USA* 1992, 89, 4505.
Petithory *Proc. Natl. Acad. Sci. USA*, 1991, 88, 11510.
Geyse *Proc. Natl. Acad. Sci. USA*, 1984, 81, 3998.
Houghten *Proc. Natl. Acad. Sci. USA*, 1985, 82, 5131.
Fodor *Science* 1991, 251, 767.
Bieber et al. *J. Antibiot.* 1987, 40, 1335.
Kolar et al. *Carbohydr. Res.* 1990, 208, 111.

Arcamone, F. *Doxorubicin Anticancer Antibiotics*; Academic Press: New York, 1981.
Suzuki et al. *J. Am. Chem. Soc.* 1990, 112, 8895.
Barany, G. and Merrifield, R.B. 1979, in *The Peptides*, Gross, E. and Meienhofer, J. Eds., Academic Press, New York, vol. 2, pp. 1–284 (Table of Contents Provided).
Frechet and Schuerch *J. Am. Chem. Soc.* 1971, 93, 492.
Frechet, *Polymer-supported Reactions in Organic Synthesis*, p. 407, P. Hodge and D.C. Sherrington, Eds., John Wiley & Sons, 1980.
Douglas et al. *J. Am. Chem. Soc.* 1991, 113, 5095–5097.
Kahne et al. *J. Am. Chem. Soc.* 1989, vol. 111, No. 17, 6881–6882.
Binkley *Modern Charbohydrate Chemistry*, Marcel Dekker, Inc: New York, 1988.
Paulsen *Angew. Chem. Int. Ed. Engl.* 1982, vol. 21, No. 3, pp. 155–173.
Ito and Ogawa *Tetrahedron Lett.* 1987, vol. 28, No. 24, 2723–2726.
Lonn *Glycoconjugate J.* 1987, 4, 117.
Mootoo et al. *J. Am. Chem. Soc.* 1989, 111, 8540.
Evans et al. *J. Am. Chem. Soc.* 1990, 112, 7001.
Veeneman et al. *Tetrahedron Lett.* 1990, 31, 1331.
Nakamura *J. Am. Chem. Soc.* 1983, 105, 7172.
Ikemoto and Schreiber *J. Am. Chem. Soc.* 1990, 112, 9657.
Horita et al. *Tetrahedron*, 1986, 42, 3021.
Oikawa et al. *Tet. Lett.* 1984, 25, 5393.
*Carbohydrates*, Ed. Collins, P.M. Chapman and Hall: New York, 1987.
Mootoo et al. *J. Am. Chem. Soc.* 1988, 110, 5583.
Veeneman and van Boom *Tet. Lett.* 1990, 31, 275.
Mehta and Pinto *Tet. lett.* 1991, 32, 4435.
Friesen and Danishefsky *J. Am. Chem. Soc.* 1989, 111, 6656.
Halcomb and Danishefsky *J. Am. Chem. Soc.* 1989, 111, 6661.
Nicolaou et al. *J. Am. Chem. Soc.* 1984, 106, 4189.
Barrett et al. *J. Am. Chem. Soc.* 1989, 111, 1392.
Martin et al. *Carbohydr. Res.* 1983, 115, 21.
Giese et al. *Angew Chem. Int. Ed. Engl.* 1987, 26, 233.
*Template Chromatography of Nucleic Aids and Proteins*, Schott, H. Marcel Dekker, Inc.: New York 1984.

(List continued on next page.)

*Primary Examiner*—Herbert J. Lilling
*Attorney, Agent, or Firm*—Lowe, Price, LeBlanc & Becker

[57] ABSTRACT

The invention relates to methods that permit the rapid construction of oligosaccharides and other glycoconjugates. Methods for forming multiple glycosidic linkages in solution in a single step are disclosed. The invention takes advantage of the discovery that the relative reactivity of glycoside residues containing anomeric sulfoxides and nucleophilic functional groups can be controlled. In another aspect of the invention, the reactivity of activated anomeric sugar sulfoxides is utilized in a solid phase method for the formation of glycosidic linkages. The methods disclosed may be applied to the preparation of specific oligosaccharides and other glycoconjugates, as well as to the preparation of glycosidic libraries comprising mixtures of various oligosaccharides, including glycoconjugates, which can be screened for biological activity.

20 Claims, 24 Drawing Sheets

OTHER PUBLICATIONS

*Glycoconjugates: Composition, Structure and Function,* Allen, H.J., Kisailus, E.C., Eds. Marcel Dekker: NY 1992.

Inhoffen et al. *Croatica Chem. Acta.* 1957, 29, 329.

Trost et al. *J. Am. Chem. Soc.* 1977, 99, 8116.

Stork and Hagedorn *J. Am. Chem. Soc.* 1978, 100, 3609.

Binkley, R.W. *Modern Carbohydrate Chemistry,* Marcel Dekker, Inc.: New York, 1988.

Ferrier et al. *Carbohydr. Res.* 1973, vol. 27, pp. 55–61.

Mukaiyama et al. *Chem. Lett.* 1979, 487.

Van Cleve *Carbohydr. Res.* 1979, 70, 161.

Hanessian et al. *Carbohydr. Res.* 1980, 80, C17.

Garegg et al. *Carbohydr. Res.* 1983, vol. 116, pp. 162–165.

Nicolaou et al. *J. Am. Chem. Soc.* 1983, vol. 105, No. 8, 2430–2433.

Ito et al. *Tetrahedron Letters,* 1987, vol. 28, No. 40, pp. 4701–4704.

Lonn, *Carbohydrate Research,* 1985, vol. 139, pp. 105–113.

Andersson et al., pp. 3919–3992, "Synthesis of 1.2 CIS–Linked Glycosides using Dimethi(methylio)Sulfonium Triflate as Promoter and Thiglycosides and Glycosyl Donors".

Ito et al., pp. 1061–1064, "Benzenseleneyl Triflate as a Promoter of Thiglycosides: A New Method for O–Glycosylation Using Thioglycosides".

Letsinger et al., *Biochemistry,* 1989, vol. 86, pp. 6553–6556.

Brown et al., *Tetahedron Letters,* 1988, vol. 29, No. 38, pp. 4873–4876.

Dasgupta et al., *Carbohydrate Research,* 1988, vol. 177, pp. c13–c17.

Gordon et al., *Proc. Natl. Acad. Sci.,* 1985, vol. 82, pp. 7419–7423.

Malinowska et al., *Proc. Natl. Acad. Sci.,* 1981, vol. 78, pp. 5908–5912.

Spigelman et al., Neurosurgery, 1983, vol. 2, No. 6, pp. 606–612.

Oehike, *Chemical Abstracts,* 94:98644b.

Kramer et al., *Chemical Abstracts,* 115:72019d.

Oehike, *Chemical Abstracts,* 92:59167n.

Oehike, *Pharmazie,* 1979, vol. 34, H.7., pp. 383–386.

Riccio et al., *J. Org. Chem.,* 1986, vol. 51, No. 4, pp. 533–536.

Exhibit A, pp. 1–8, claims 1–5, 7–8, 14, 19, 51–53, 56–75, and 77–82.

Gerald F. Joyce, *Scientific American,* 1992, Dec., pp. 90–97.

Ito et al., Tetrahedron Letters, 1988, vol. 29, No. 9, pp. 1061–1064.

Kuhn et al., *Chemical Abstracts,* May 25, 1992, 116; 214811 No. 21.

Abstract, Lieb 165 Ann Chem 1992 (4) 407–9.

Ginsburg et al., *Academic Press (Boston),* 1987, vol. 138, Part E.

*Carbohydrate Research,* 1992, vol. 233, pp. 245–250.

SCHEME 1 PREMIXED 1(3.0eq), 2(2.0eq) AND 3(1.0eq), Et₂O-CH₂Cl₂(1:1), HC≡CCOOCH₃(20eq), TfOH(0.05eq), -78°C TO -70°C, 45MIN, THEN QUENCHED WITH SAT. NaHCO₃ SOLUTION.

A. REACTOR SETUP FOR ATTACHMENT OF LINKING SUGAR AND GLYCOSYLATION

B. REACTOR SETUP FOR WASHING AND FILTRATION.

SINGLE-STEP FORMATION OF MULTIPLE GLYCOSIDIC LINKAGES

1. FIELD OF THE INVENTION

The present invention relates generally to methods that permit the rapid construction of oligosaccharides and other glycoconjugates. More particularly, the present invention relates to methods for forming multiple glycosidic linkages in solution in a single step. The present invention takes advantage of the discovery that the relative reactivity of glycoside residues containing anomeric sulfoxides and nucleophilic functional groups can be controlled. In another aspect of the present invention, the reactivity of activated anomeric sugar sulfoxides is utilized in a solid phase method for the formation of glycosidic linkages. The methods disclosed may be applied to the preparation of specific oligosaccharides and other glycoconjugates, as well as to the preparation of glycosidic libraries comprising mixtures of various oligosaccharides, including glycoconjugates, which can be screened for biological activity.

2. BACKGROUND OF THE INVENTION

2.1. General Background

The oligosaccharide chains of glycoproteins and glycolipids play important roles in a wide variety of biochemical processes. Found both at cell surfaces and circulating in biological fluids, these glycosidic residues act as recognition signals that mediate key events in normal cellular development and function. They are involved in fertilization, embryogenesis, neuronal development, hormonal activities, inflammation, cellular proliferation, and the organization of different cell types into specific tissues. They are also involved in intracellular sorting and secretion of glycoproteins as well as in the clearance of plasma glycoproteins from circulation.

In addition to their positive role in the maintenance of health, oligosaccharides are also involved in the onset of disease. For instance, oligosaccharides on cell surfaces function as receptors for viruses and toxins, as well as more benign ligands. Modified cell surface carbohydrates have been implicated in tumorigenesis and metastasis. The oligosaccharide structures that mediate inflammation and help prevent infection can, when produced at excessive levels, stimulate the development of chronic inflammatory disease. (Some references on the roles of oligosaccharides produced by eukaryotes in health and disease include: Hakomori, S. TIBS, 1984, 45; Feizi, T., et al., TIBS, 1985, 24; Rademacher, T. W. et al., *Annu. Rev. Biochem.* 1988, 57, 785; Feizi, T. TIBS, 1991, 84; Dennis, J. W.; Laferte, S. *Cancer Res.* 1985, 45, 6034; Fishman, P. H. J. *Membr. Biol.* 1982, 69, 85; Markwell, M. A. et al. *PNAS USA*, 1981, 78, 5406; Wiley, D. C.; Skehel, J. *J. Annu. Rev. Biochem.* 1987, 56, 365; Kleinman, H. et al. *PNAS USA*, 1979, 76, 3367; Walz, G.; Aruffo, A.; Kolanus, W.; Bevilacqua, M , Seed, B. *Science* 1990, 250.)

Although bacteria do not produce the same types of oligosaccharides or other glycoconjugates as eukaryotes, procaryotes nevertheless produce a wide variety of glycosylated molecules. Many such molecules have been isolated and found to have antitumor or antibiotic activity. Bacterially produced glycosylated molecules having potential therapeutic utility include chromomycin, calicheamicin, esperamicin, and the ciclamycins. In all these cases, the carbohydrates residues have been shown to be important to biological activity. However, the precise functions of the carbohydrate residues are not well understood and there is no understanding of structure-activity relationships.

Because of their diverse roles in health and disease, oligosaccharides have become a major focus of research. It is widely accepted that the development of technology to 1) detect and 2) block or otherwise regulate some of the abnormal functions of oligosaccharides would lead to significant improvements in health and well-being. Moreover, it should be possible to exploit some of the normal functions of oligosaccharides (e.g., various recognition processes) for other purposes, including drug delivery to specific cell types. In addition, it may be possible to develop new antitumor agents from synthetic glycosylated molecules reminiscent of glycosylated bacterial antitumor agents.

There are ongoing efforts to develop products related to oligosaccharides, including diagnostic kits for detecting carbohydrates associated with various diseases, vaccines to block infection by viruses that recognize cell surface carbohydrates, drug delivery vehicles that recognize carbohydrate receptors, and monoclonal antibodies, which recognize abnormal carbohydrates, for use as drugs. The timely development of these and other carbohydrate-based biomedical products depends in turn on the availability of technology to produce oligosaccharides and other glycoconjugates rapidly, efficiently, and in practical quantities for basic and developmental research.

In particular, there is a need for methods that permit the rapid preparation of glycosidic libraries comprising mixtures of various oligosaccharides or other glycoconjugates which could then be screened for a particular biological activity. It has been shown, for example, that screening of mixtures of peptides is an efficient way of identifying active compounds and elucidating structure-activity relationships. There are numerous ways to generate chemically diverse mixtures of peptides and determine active compounds (See, for example, Furka et al. *Int. J. Peptide Protein Res.* 1992, 37, 487; Lam et al. *Nature* 1991, 354, 82; Houghten, R. A. *Nature* 1991, 354, 84; Zuckermann, R. N. et al. *Proc. Natl. Acad. Sci. USA* 1992, 89, 4505. Petithory, J. R. *Proc. Natl. Acad. Sci. USA*, 1991, 88, 11510. Geyse, H. M. et al. *Proc. Natl. Acad. Sci. USA*, 1984, 81, 3998. Houghten, R. A.; *Proc. Natl. Acad. Sci. USA*, 1985, 82, 5131; Fodor et al. *Science* 1991, 251, 767.) We are not aware of effective methods to generate diverse mixtures of oligosaccharides and other glycoconjugates for screening purposes.

2.2. Solution Methods For Obtaining Oligosaccharides

There are currently two general ways to obtain oligosaccharides. The first is by isolation from natural sources. This approach is limited to naturally occurring oligosaccharides that are produced in large quantities. The second way is through enzymatic or chemical synthesis. The variety of oligosaccharides available through enzymatic synthesis is limited because the enzymes used can only accept certain substrates. Chemical synthesis is more flexible than enzymatic synthesis and has the potential to produce an enormous variety of oligosaccharides. The problem with chemical synthesis has been that it is extremely expensive in terms of time and labor. This problem is a consequence of the way in which the chemical synthesis of oligosaccharides has been carried out to date.

Oligosaccharides are formed from monosaccharides connected by glycosidic linkages. In a typical chemical synthesis of an oligosaccharide, a fully protected glycosyl donor is activated and allowed to react with a glycosyl acceptor (typically another monosaccharide having an unprotected hydroxyl group) in solution. The glycosylation reaction itself can take anywhere from a few minutes to days, depending on the method used. The coupled product is then purified and chemically modified to transform it into a glycosyl donor. The chemical modification may involve several steps, each single step requiring a subsequent purification. (A "single step" is defined as a chemical transformation or set of transformations carried out in a "single" reaction vessel without the need for intermediate isolation or purification steps.) Each purification is time consuming and can result in significant losses of material. The new glycosyl donor, a disaccharide, is then coupled to another glycosyl acceptor. The product is then isolated and chemically modified as before. It is not unusual for the synthesis of a trisaccharide to require ten or more steps from the component monosaccharides. In one recent example (See, Suzuki, K. et al. *J. Am. Chem. Soc.* 1990, 112, 8895.), the fully protected trisaccharide side chain of an antitumor antibiotic called ciclamycin 0 was synthesized in 14 steps with a 9% yield based on the component monosaccharides. Thus, the time and expense involved in the synthesis of oligosaccharides has been a serious obstacle to the development of carbohydrate drugs and other biomedical products.

One way to increase the speed and efficiency of oligosaccharide synthesis is to develop methods that permit the construction of multiple glycosidic linkages in a single step. Before the present discovery, the applicants are unaware of a one-step method which involves the regioselective formation of multiple glycosidic bonds and which provides a rapid, efficient and high yield process for the production of oligosaccharides.

2.3. Solid-Phase Synthesis Of Oligosaccharides

Besides reducing the number of steps involved in the synthesis of oligosaccharides, one can also increase the speed and efficiency of a synthetic process by eliminating the need for isolation and purification. Theoretically, elimination of the need for isolation and purification could be achieved by developing a solid-phase process for the synthesize of oligosaccharides.

Due to the magnitude of the potential advantages of solid-phase synthesis, there have been previous attempts to synthesize oligosaccharides on a solid phase. Solid-phase methods for synthesis make isolation and purification unnecessary because excess reagents and decomposition products can simply be washed away from the resin-bound product. This advantage translates into an enormous savings in terms of time, labor, and yield. (The advantages of solid-phase methods over solution methods for the synthesis of peptides and nucleic acids have been amply demonstrated. These advantages would, of course, extend to a solid-phase synthesis of oligosaccharides. For the solid-phase synthesis of peptides, see, for example, Barany, G. and Merrifield, R. B. 1980, in *The Peptides*, Gross, E. and Meienhofer, J. Eds., Academic Press, New York, Vol 2, pp. 1–284.)

As far back as 1971, Frechet and Schuerch outlined the requirements for solid-phase oligosaccharide synthesis (Frechet, J. M.; Schuerch, C.; *J. Am. Chem. Soc.* 1971, 93,492). First, the resin must be compatible with the reaction conditions. Second, the solid support must contain appropriate functionality to provide a link to the glycosidic center (or elsewhere), which link is inert to the reaction conditions but can be easily cleaved to remove the oligosaccharide upon completion of the synthesis. Third, appropriate protecting group schemes must be worked out so that particular hydroxyls can be selectively unmasked for the next coupling reaction. The other hydroxyls should be protected by "permanent" blocking groups to be removed at the end of the synthesis. Fourth, the glycosylation reactions should be efficient, mild, and go to completion to avoid failure sequences. Fifth, the stereochemistry of the anomeric centers must be maintained during the coupling cycles and should be predictable based on the results obtained in solution for any given donor/acceptor pair. Sixth, cleavage of the permanent blocking groups and the link to the polymer must leave the oligosaccharide intact.

Unfortunately, although it has been generally accepted that solid-phase oligosaccharide synthesis is a desirable goal, and although Frechet and Schuerch (as well as others) were able to outline a strategy for solid-phase oligosaccharide synthesis, no one, before the present discovery, had been able to implement such a strategy. In previous attempts to synthesize oligosaccharides on insoluble resins, the coupling yields were low and the stereochemical control was inadequate, particularly for the construction of β-glycosidic linkages (i.e., 1,2-trans glycosidic linkages in which the glycosidic bond at the anomeric position of the sugar is trans to the bond bearing the sugar substituent at C-2).

These problems have been attributed to the fact that reaction kinetics on the solid phase are slower than they are in solution. (See, Eby and Schuerch, *Carbohydr. Res.* 1975, 39, 151.) The consequence of such unfavorable kinetics is that most glycosylation reactions, which may work reasonably well in solution, simply do not work well on a solid phase both in terms of stereochemical control and yield. Thus, for example, Frechet and Schuerch found that two glycosylation reactions, which both involve the displacement of an anomeric halide in the presence of a catalyst, gave predominantly the β-anomer (i.e., the 1,2-trans product) in solution but gave mixtures on the solid phase. Frechet and Schuerch concluded that it would be necessary to use neighboring group participation to form β-glycosidic linkages on the solid phase.

Again, however, it has been found that neighboring participating groups (NPGs) frequently deactivate glycosyl donors to the point that existing glycosylation methods could not be adapted to the solid phase. Frequently, glycosyl donors would decompose in the resin mixture before glycosylation can take place (See, Eby and Schuerch, *Carbohydr Res.* 1975, 39, 151). In some instances the resin has also been known to decompose due to the harshness of the conditions required for glycosylation. Furthermore, for many ester-type NPGs, there is a significant problem with acyl transfer from the glycosyl donors to the free glycosyl acceptors on the resin. This side reaction caps the resin and prevents further reaction.

Frechet has reviewed the problems encountered in trying to implement a strategy for solid-phase oligosaccharide synthesis (Frechet, *Polymer-supported Reactions in Organic Synthesis*, p. 407, P. Hodge and D. C. Sherrington, Eds., John Wiley & Sons, 1980). He has concluded that solid-phase oligosaccharide synthesis is not yet competitive with solution synthesis "due mainly to the lack of suitable glycosylation reactions."

There have been some efforts to overcome the unfavorable reaction kinetics associated with solid-phase reactions by using soluble resins. In the best example to date Douglas et al. used a soluble polyethylene glycol resin with a succinic acid linker and achieved 85–95% coupling yields using a glycosylation method known for over 80 years (the Koenigs-Knorr reaction) with excellent control of anomeric stereochemistry (Douglas, S. P.; Whitfield, D. M.; Krepinsky, J. J. *J. Am. Chem. Soc.* 1991, 113, 5095). Soluble resins may have advantages for some glycosylation reactions because they offer a more "solution-like" environment. However, step-wise synthesis on soluble polymers requires that the intermediate be precipitated after each step and crystallized before another sugar residue can be coupled.

Moreover, several additions of the same glycosylating reagent are typically required to push a reaction to completion. In the above case, for example, Douglas et al. had to repeat the same coupling reaction five times to achieve a high yield. Each repetition requires a precipitation step to wash the reagents away. Product may may be lost with each precipitation step. In addition, repeated precipitations make the process very time-consuming. Thus, the soluble resin approach to oligosaccharide synthesis fails to provide all the potential advantages associated with solid phase synthesis using insoluble resins.

A new method for glycosylation involving anomeric sugar sulfoxides was reported by Kahne and co-workers (Kahne, D. et al. *J. Am. Chem. Soc.* 1989, 111, 6881). The anomeric sugar sulfoxides were activated with equimolar amounts of triflic anhydride in the presence of a hindered base. The triflic anhydride-activated glycosyl donors proved to be quite reactive in solution and could be used to glycosylate extremely unreactive substrates under mild conditions. However, this report was limited to solution reactions, and there was no suggestion that solid-phase reactions could be carried out with any degree of utility.

Thus, the state of the art underscores the prevailing and unfullfilled need for a glycosylation method which provides for the rapid, efficient, and high yield synthesis of oligosaccharides. Moreover, an efficient synthesis of oligosaccharides on the solid phase has not been demonstrated which provides all the previously mentioned advantages of solid-phase methods.

3. SUMMARY OF THE INVENTION

The present invention provides methods for constructing multiple glycosidic linkages in solution using anomeric sugar sulfoxides as glycosyl donors and for constructing sequential glycosidic linkages on the solid phase, with control over the stereochemical configuration of the anomeric bond. Thus, depending upon the selected conditions and starting materials, α- or β-anomers can be produced on the solid phase using anomeric sugar sulfoxides as glycosyl donors. The methods of the present invention may be applied to the preparation of specific oligosaccharides or glycoconjugates or to the preparation of mixtures of various oligosaccharides or glycoconjugates for the creation of glycosidic libraries that can subsequently be screened to detect compounds having a preselected biological activity.

4. BRIEF DESCRIPTION OF THE FIGURES

Figure 1:
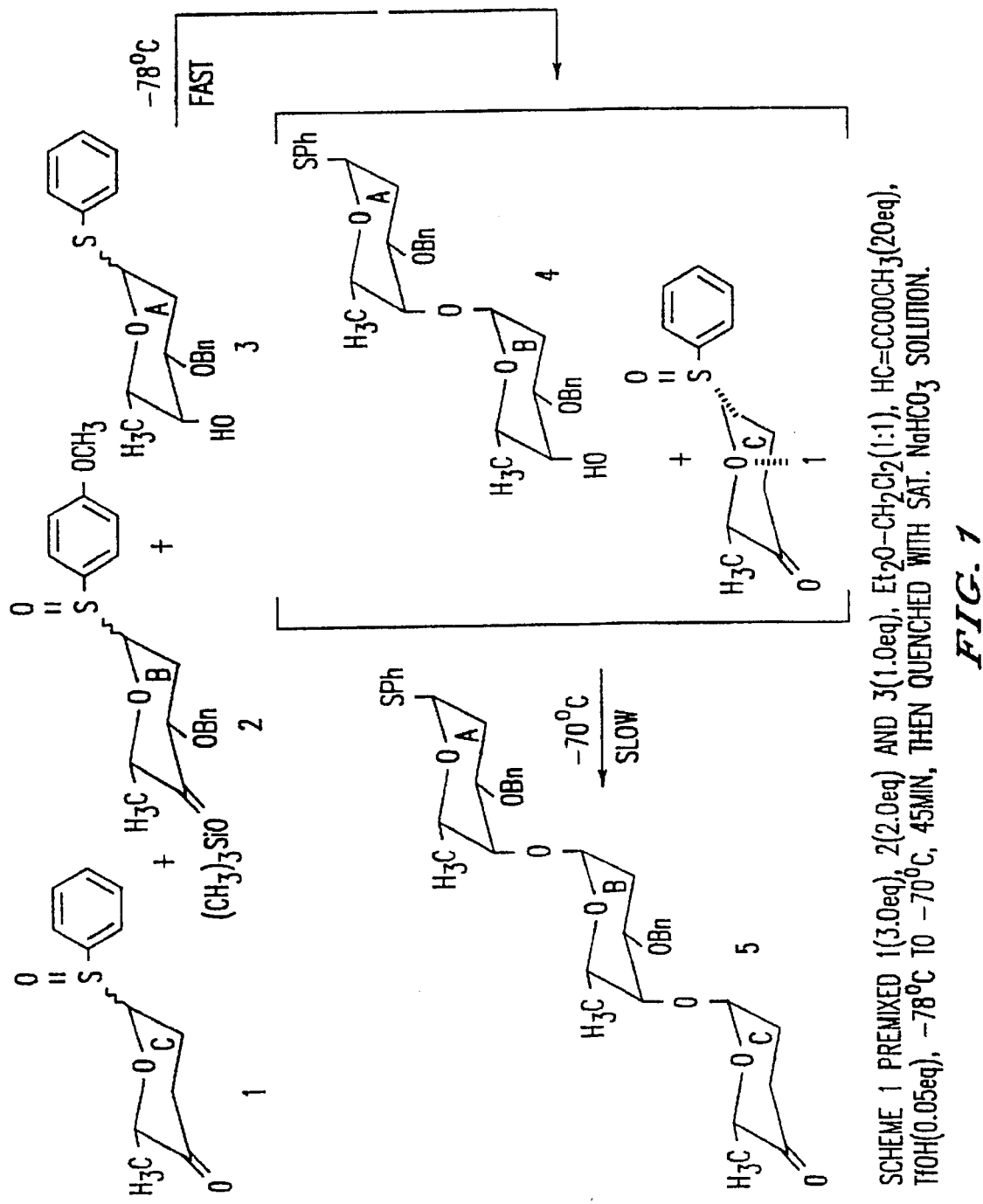
FIG. 1 illustrates a method of synthesizing the protected trisaccharide of ciclamycin 0 in one step from the component monosaccharides.
Figure 9:
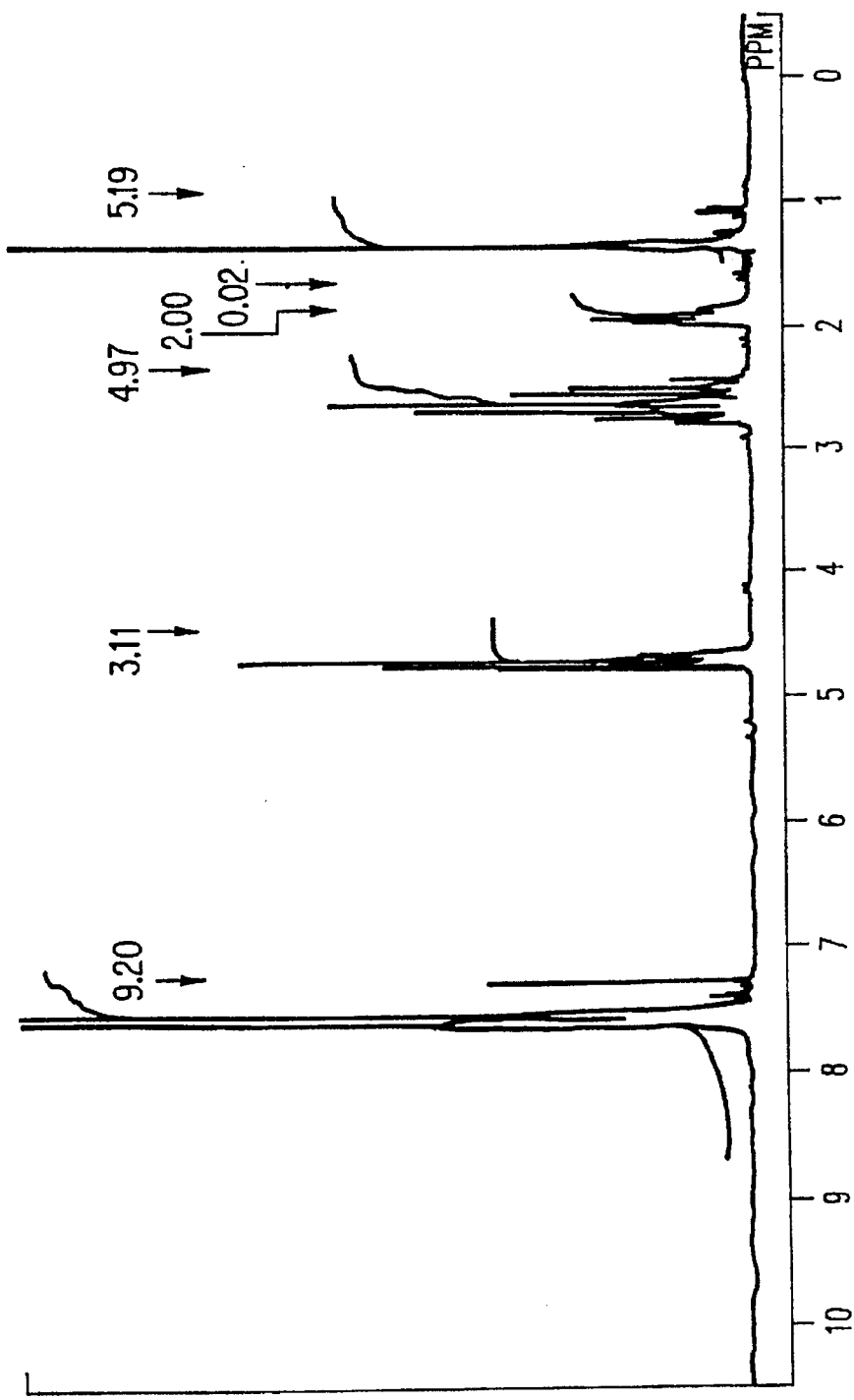

FIG. 9 presents the proton NMR spectrum of the monosaccharide 1 of FIG. 1.

Figure 10:
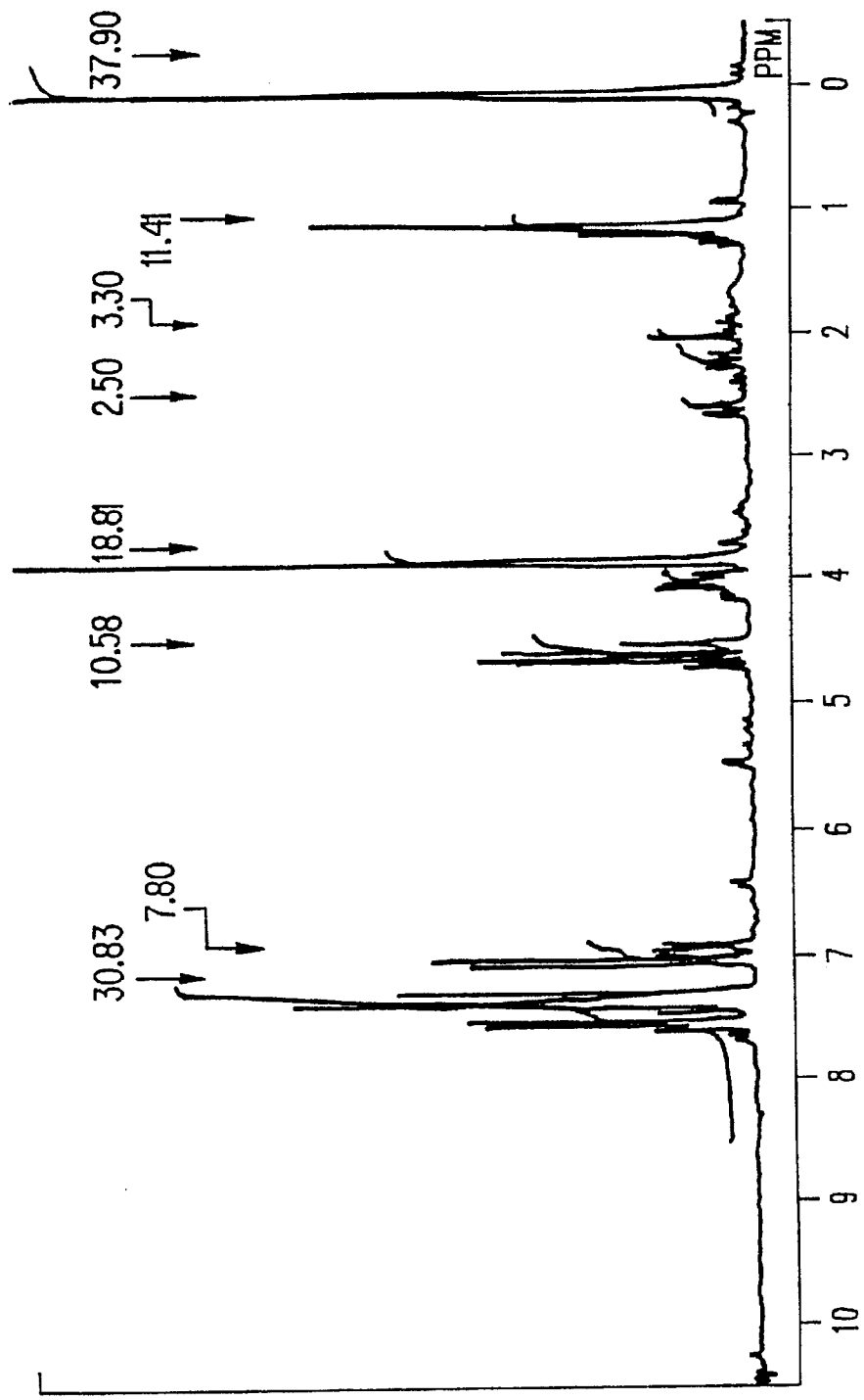

FIG. 10 presents a proton NMR spectrum of monosaccharide 2 of FIG. 1.

Figure 11:
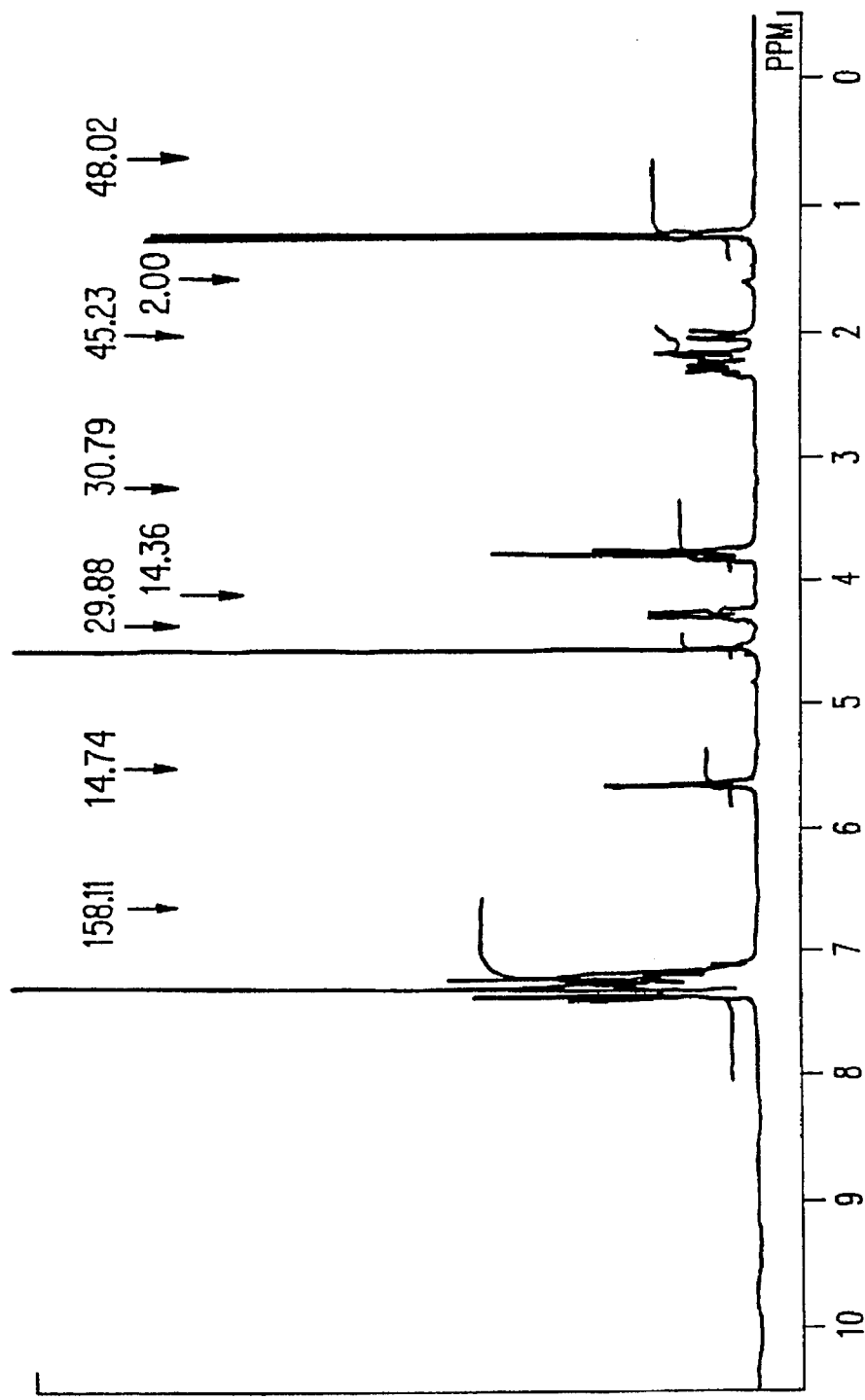

FIG. 11 presents a proton NMR spectrum of monosaccharide 3 of FIG. 1.

Figure 12:
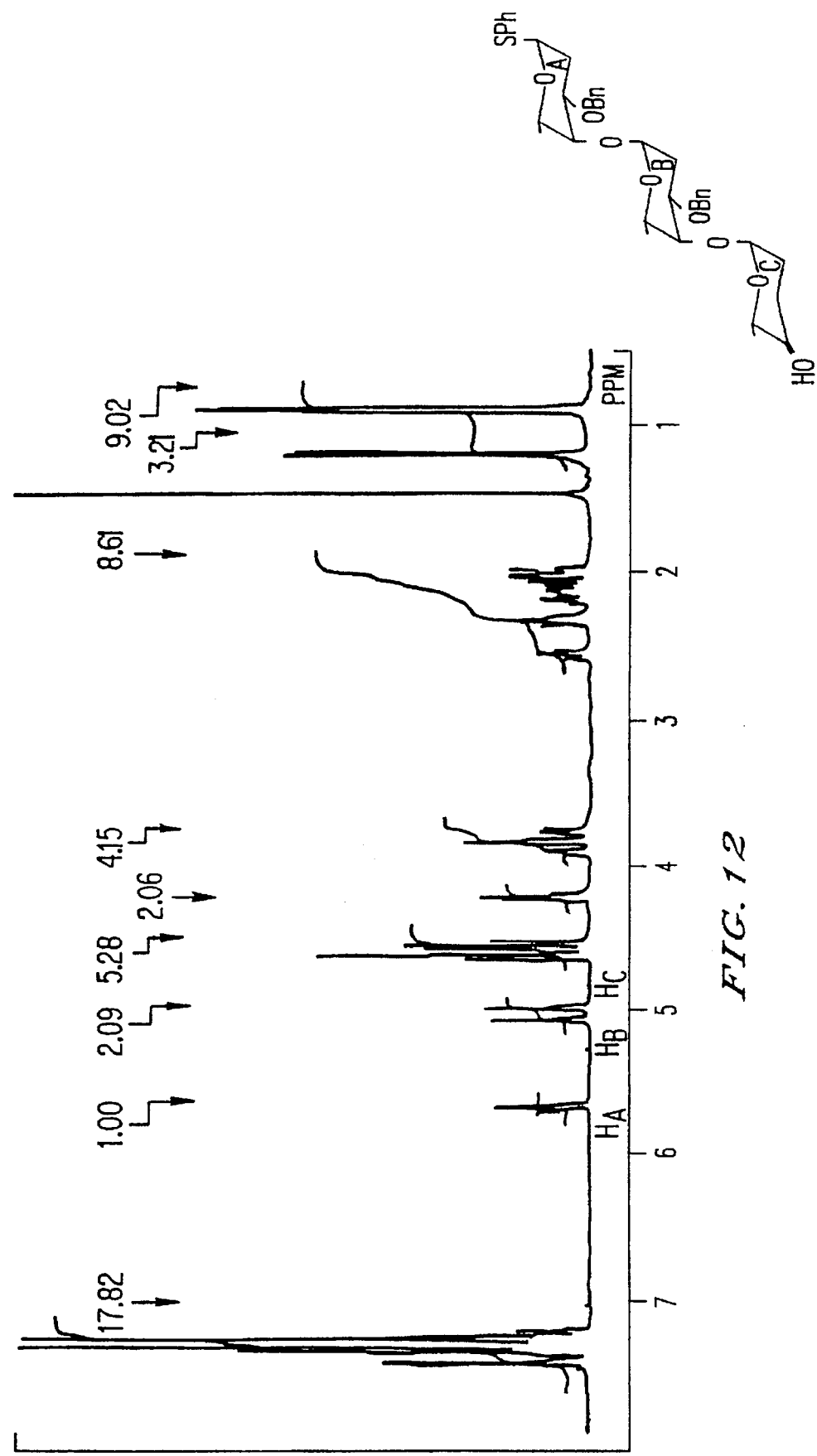

FIG. 12 presents a proton NMR spectrum of trisaccharide 5 of FIG. 1.

Figure 13:
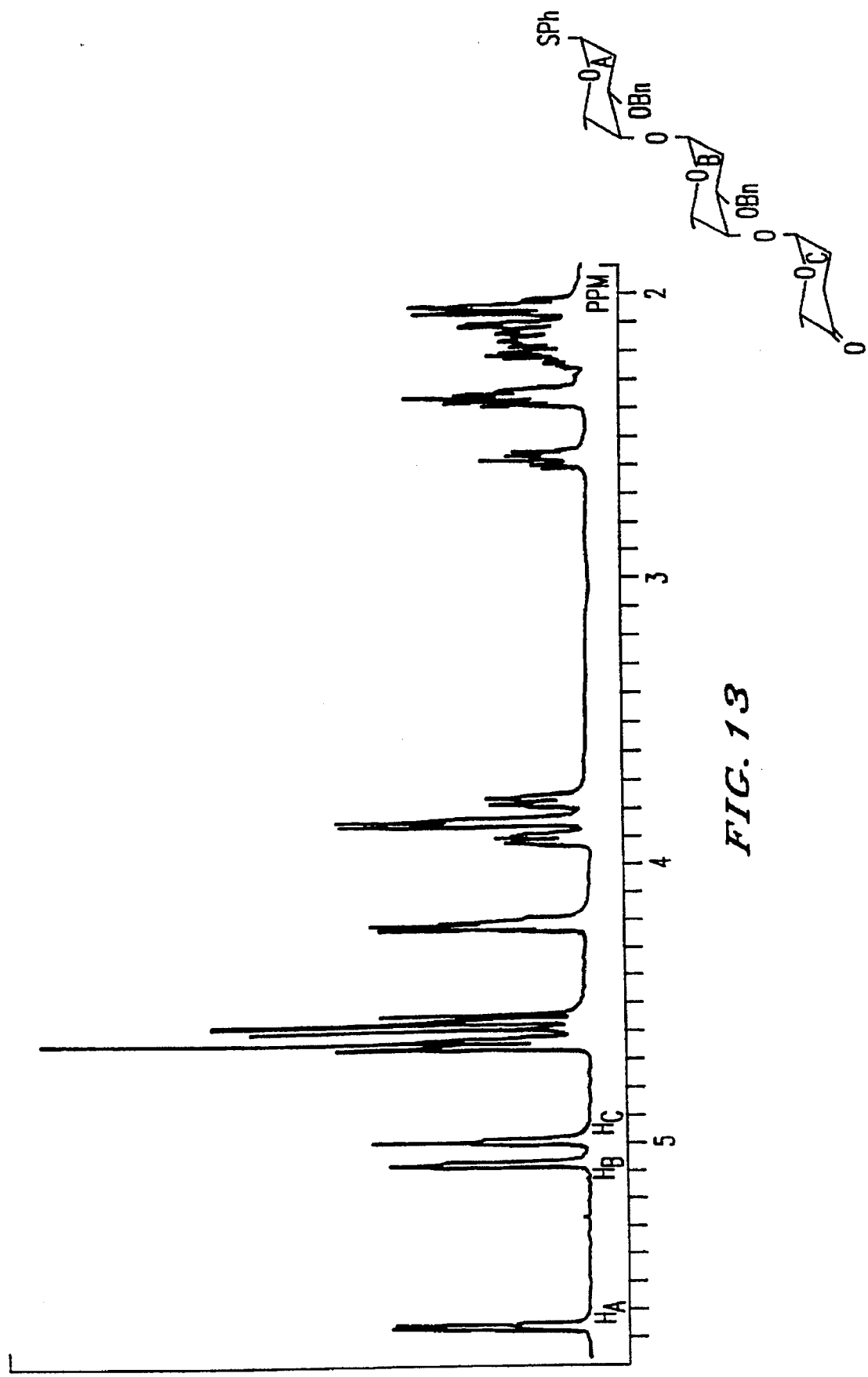

FIG. 13 presents an expanded region of the proton NMR spectrum of trisaccharide 5, in which anomeric protons of the trisaccharide are labeled.

Figure 14:
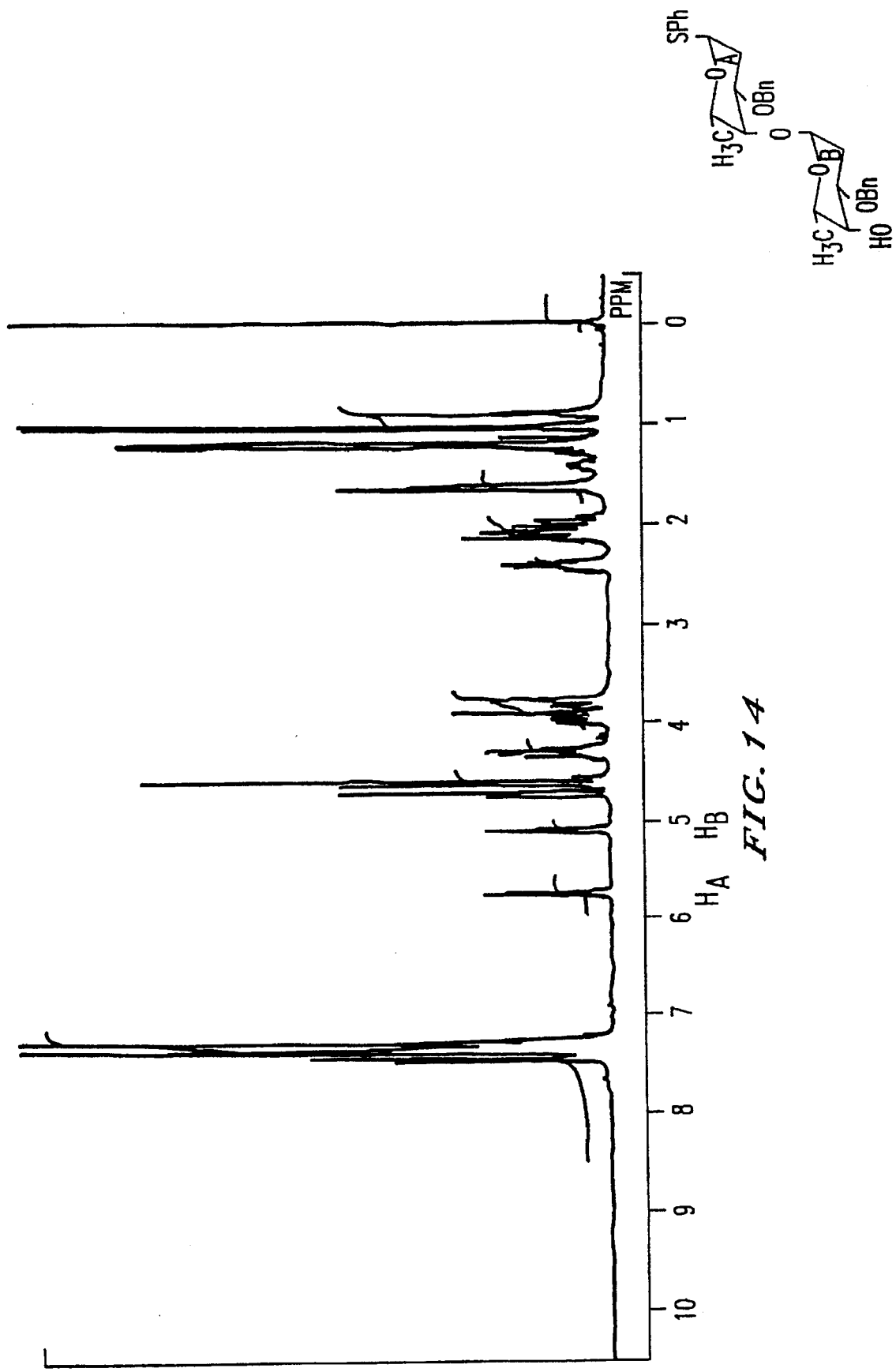

FIG. 14 presents a proton NMR spectrum of disaccharide 4 of FIG. 1.

Figure 2:
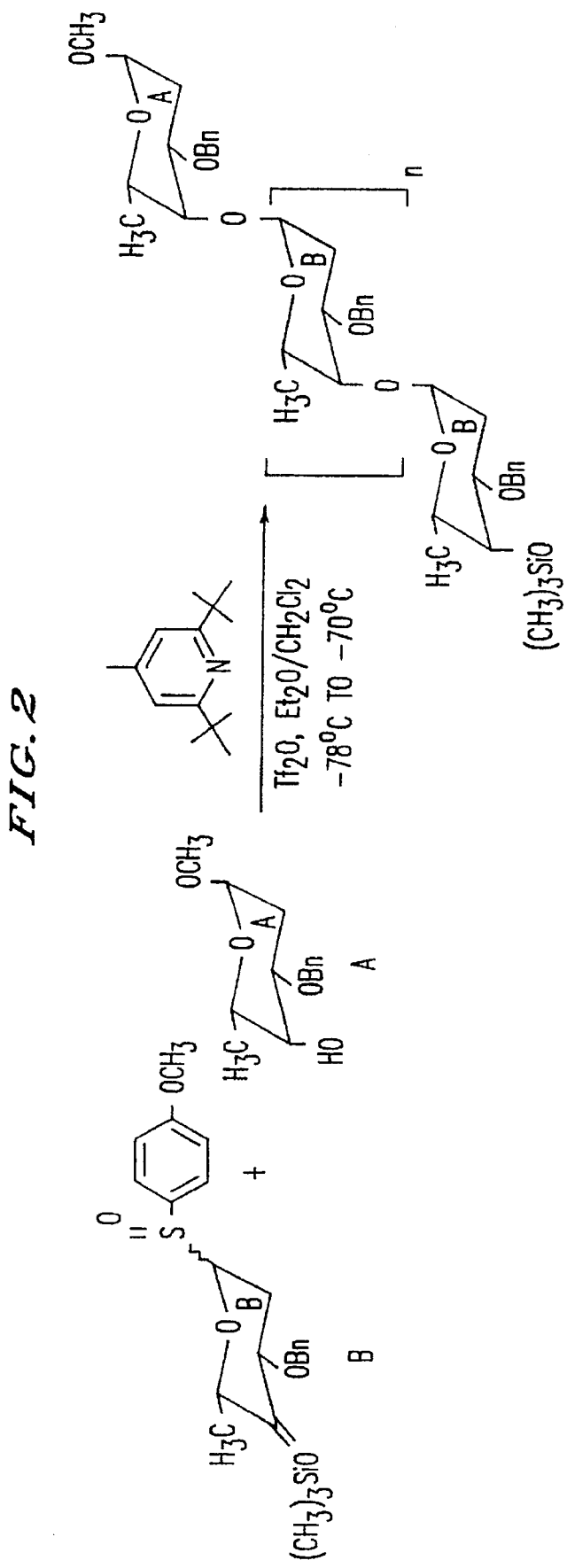
FIG. 2 illustrates a process of forming homopolymers of 2-deoxy fucose in one step.
Figure 15:
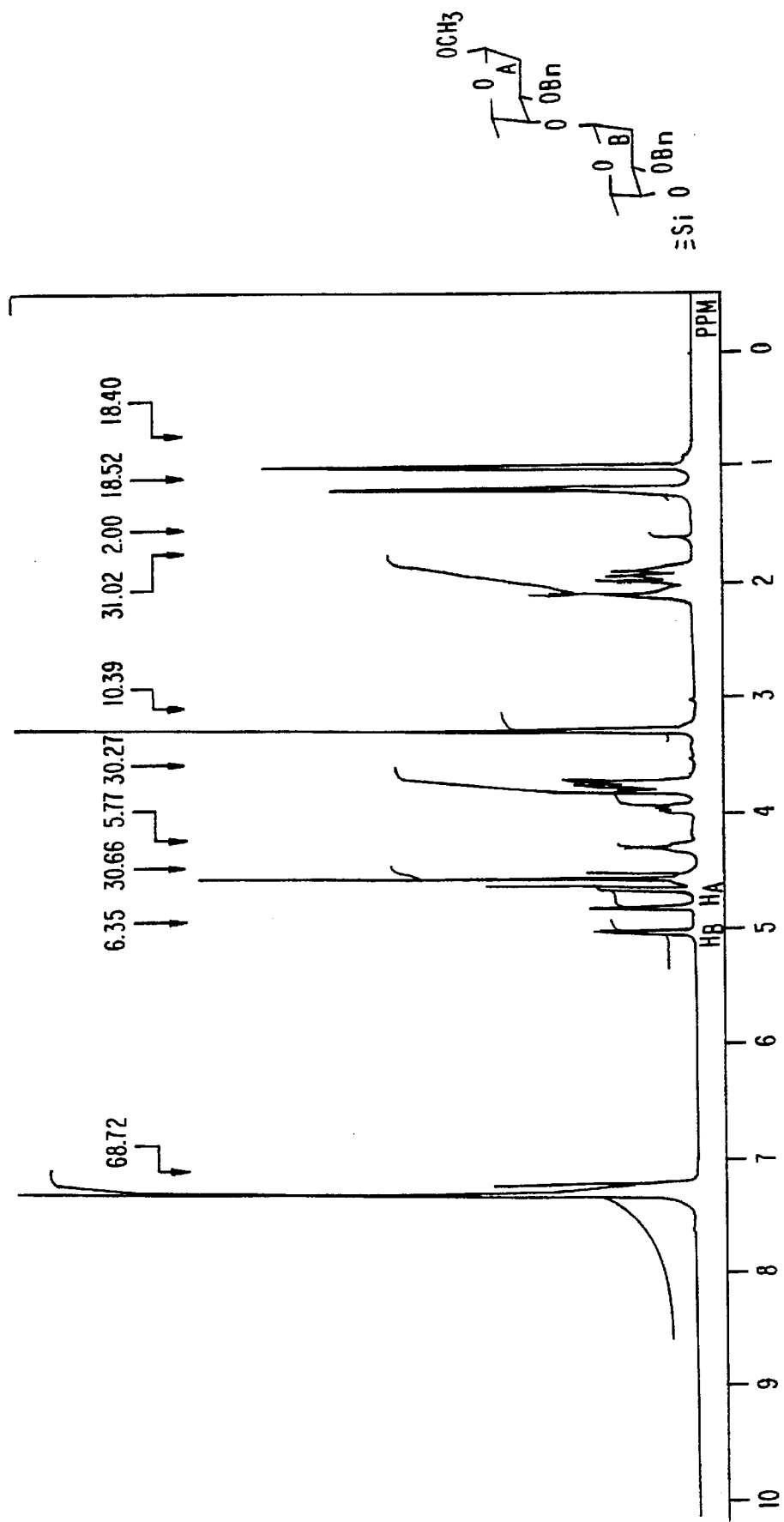

FIG. 15 presents a proton NMR spectrum of the disaccharide product of FIG. 2 in which n equals 0.

Figure 16:
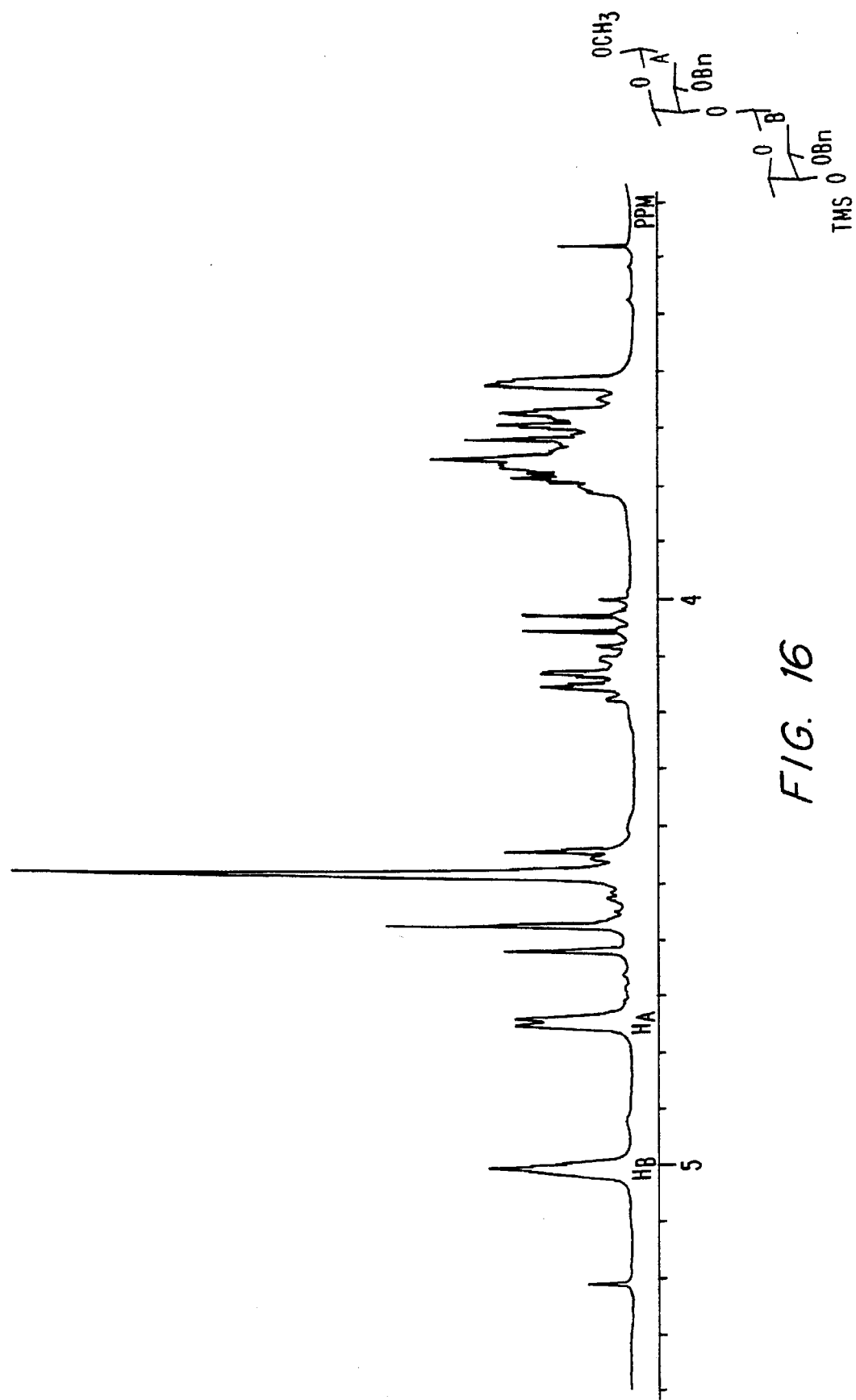

FIG. 16 presents an expanded region of the proton NMR spectrum of the disaccharide of FIG. 15 in which the anomeric protons are labeled.

Figure 17:
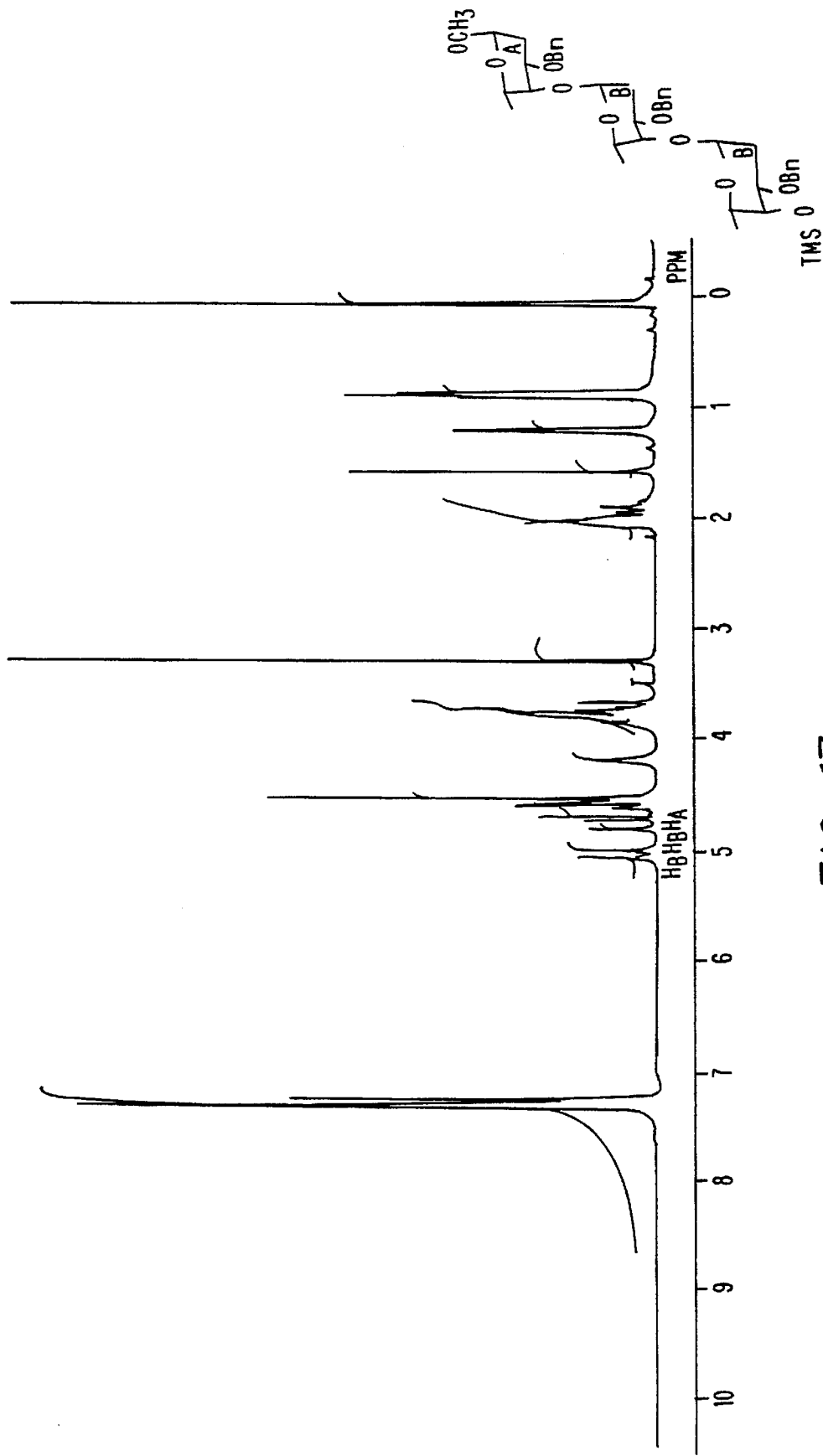

FIG. 17 presents the proton NMR spectrum of the trisaccharide product of FIG. 2 in which n equals 1.

Figure 18:
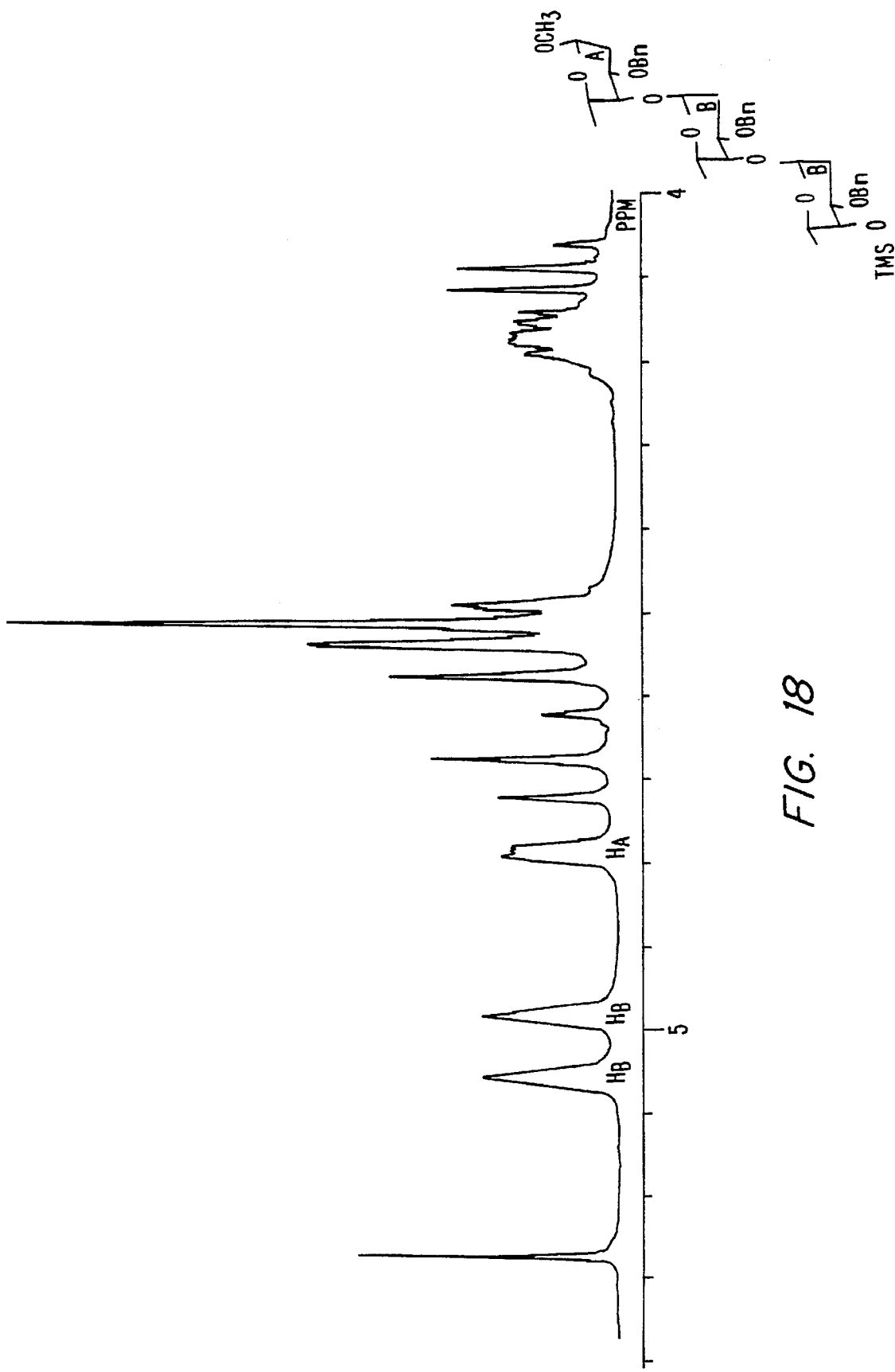

FIG. 18 presents an expanded region of the proton NMR spectrum of the trisaccharide of FIG. 17 in which the anomeric protons are labeled.

Figure 19:
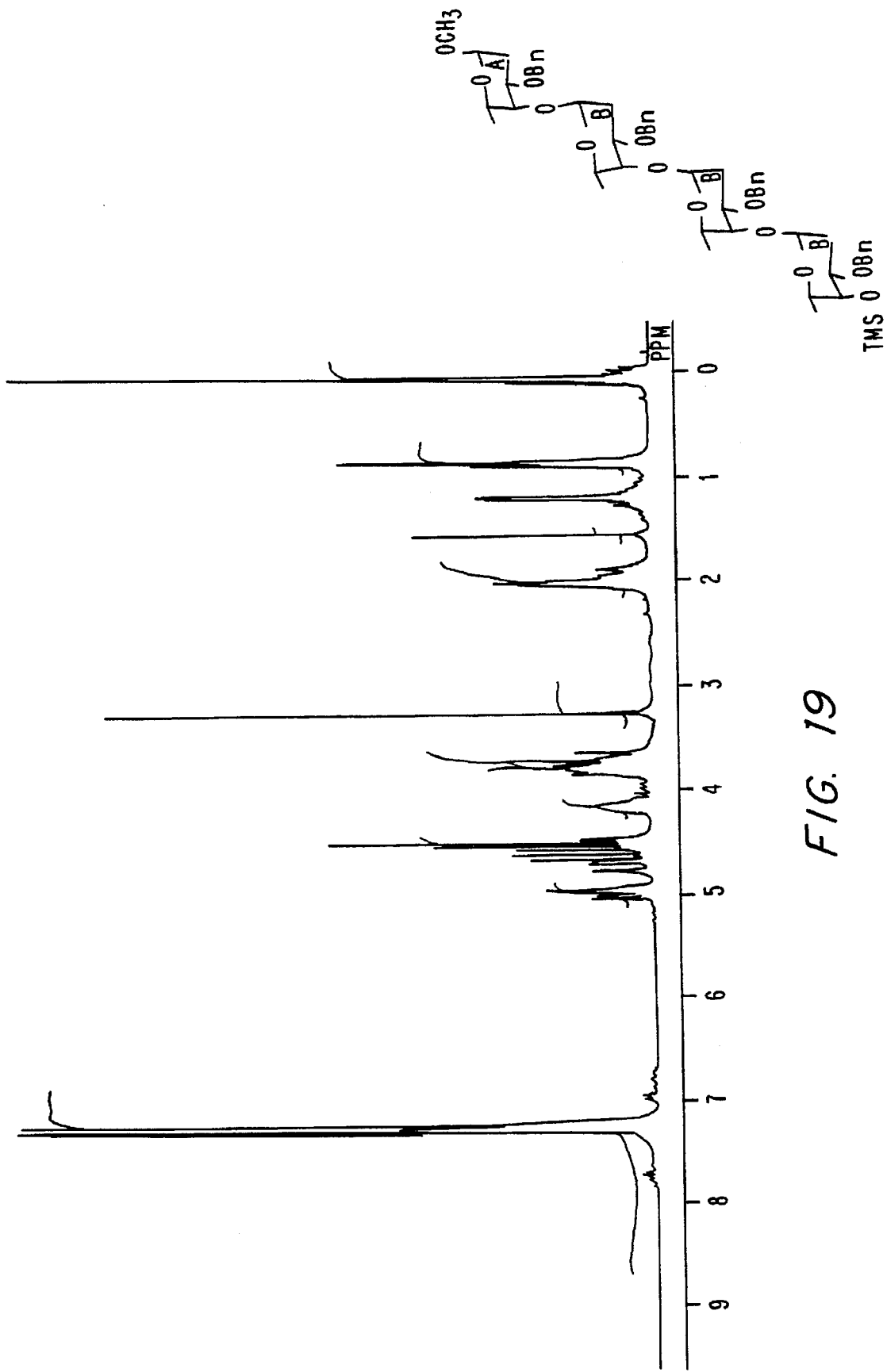

FIG. 19 presents the proton NMR spectrum of the tetrasaccharide product of FIG. 2 in which n equals 2.

Figure 20:
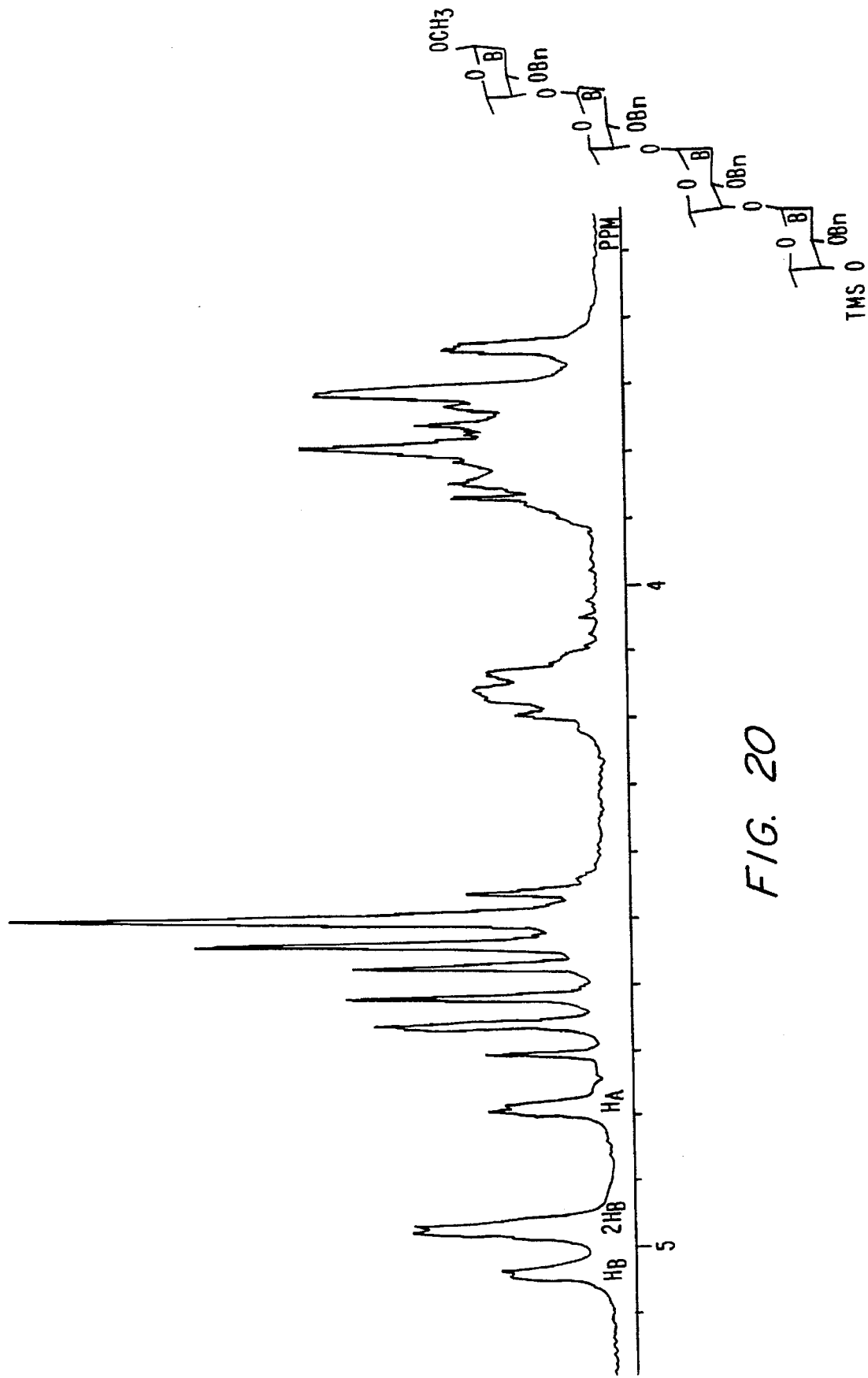

FIG. 20 presents an expanded region of the proton NMR spectrum of the tetrasaccharide of FIG. 19 in which the anomeric protons are labeled.

Figure 21:
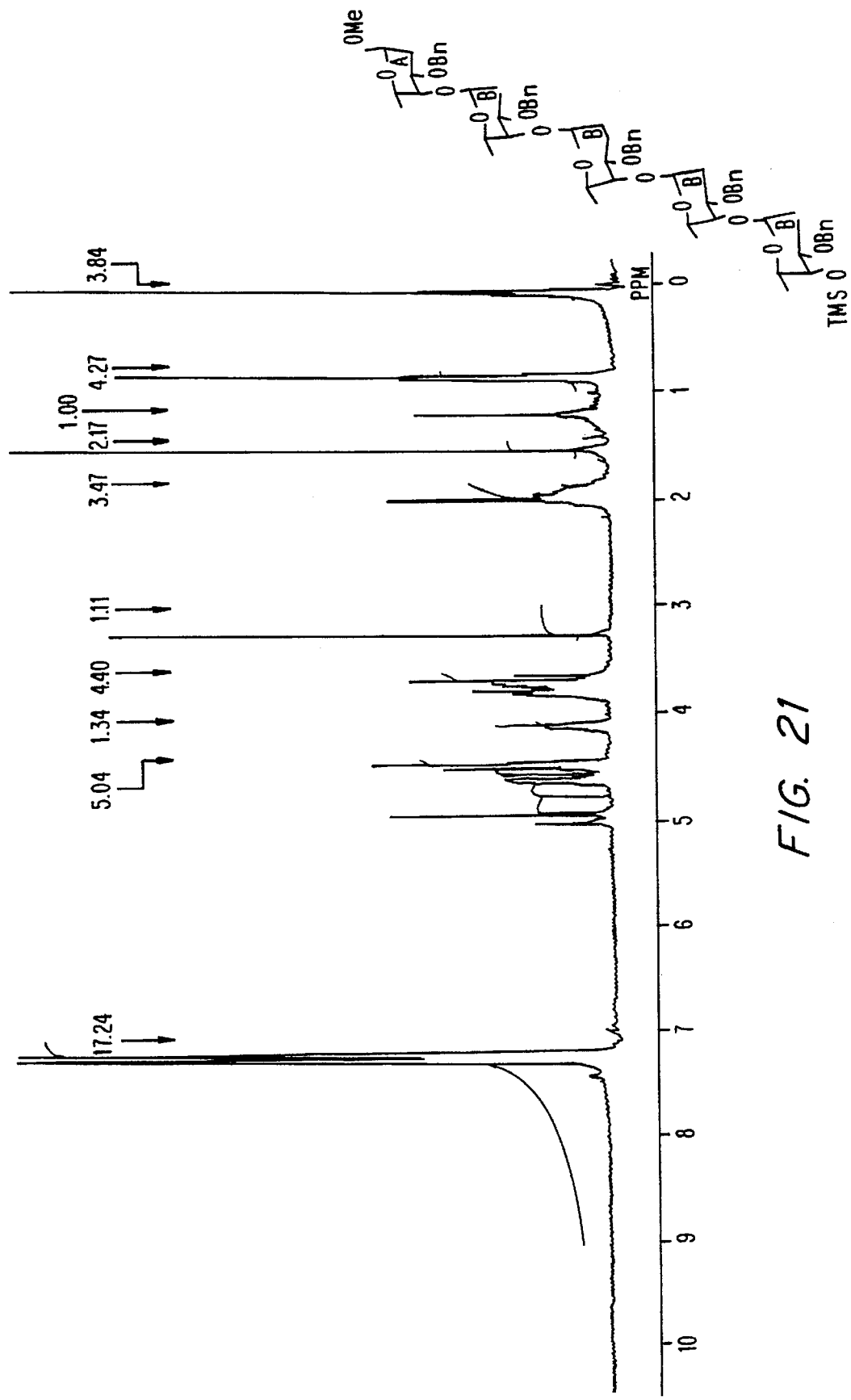

FIG. 21 presents the proton NMR spectrum of the pentasaccharide product of FIG. 2 in which n equals 3.

Figure 22:
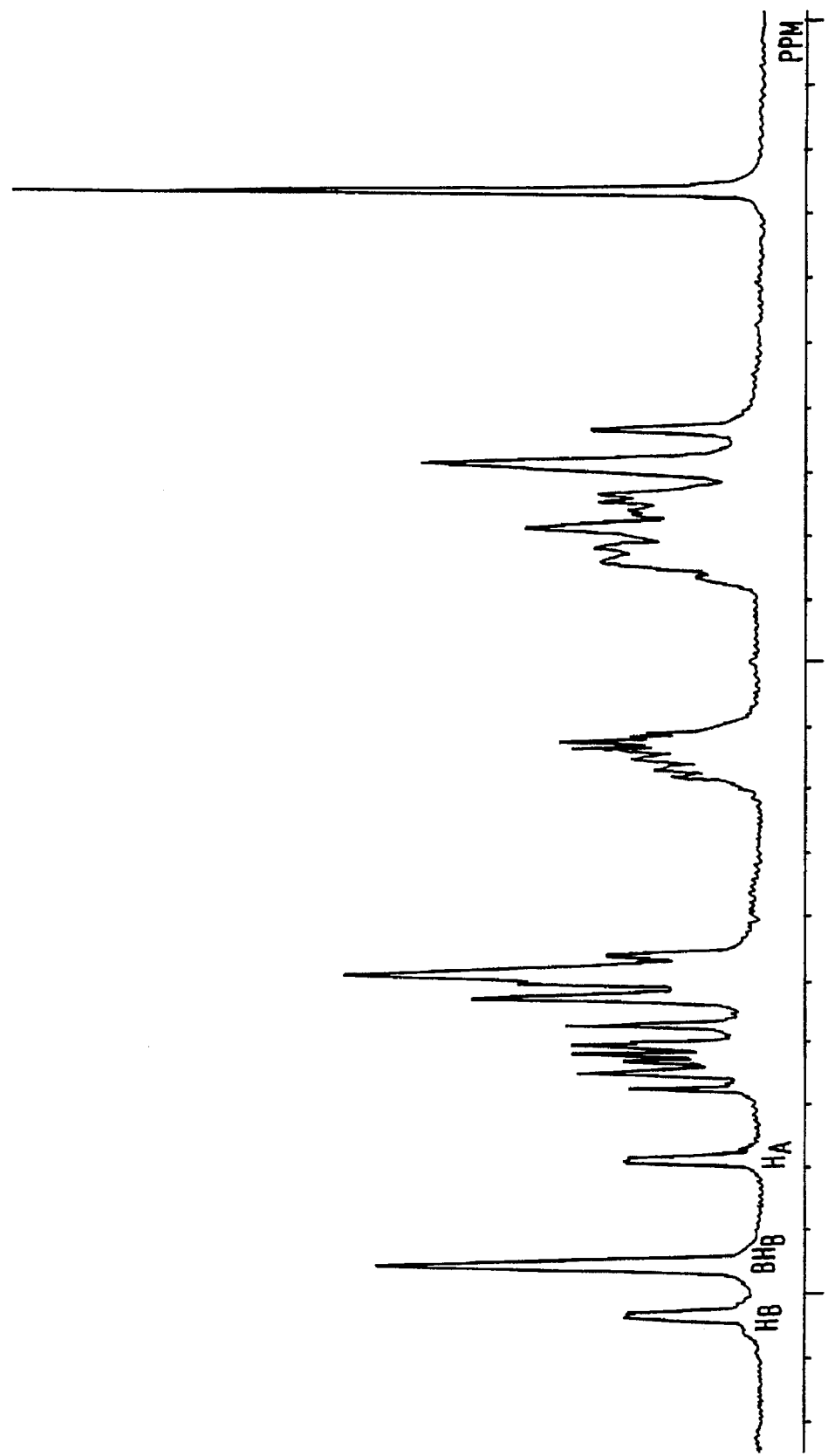

FIG. 22 presents an expanded region of the proton NMR spectrum of the pentasaccharide of FIG. 21 in which the anomeric protons are labeled.

5. DETAILED DESCRIPTION OF THE INVENTION

What follows is a detailed description of the preferred embodiments of the present invention.

5.1. Definitions

Activating agent: A chemical agent that on addition to a glycosyl sulfoxide reacts with the anomeric sulfoxide group, thus rendering the anomeric carbon susceptible to nucleophilic attack. In the case of bifunctional sugars or glycosidic residues, the activating agent is also able to deprotect a blocked nucleophilic group under the same conditions used to activate the anomeric sulfoxide group.

Acid scavenger: A chemical agent such as any base that sequesters protons, thereby minimizing side reactions that are promoted by acidic conditions.

Sulfenic acid scavenger: A chemical agent such as methyl propiolate that specifically sequesters sulfenic acid, typically resulting in the formation of an unreactive monophenyl sulfoxide. In the absence of a sulfenic acid scavenger, sulfenic acid reacts with itself to form diphenyl disulfide monosulfoxide and water. Water interferes with the glycosylation reaction.

Bifunctional: The characteristic of a sugar or glycosidic residue to be able to function on activation both as a glycosyl donor and a glycosyl acceptor under the conditions of the single-step process of the present invention.

Biological activity: Any activity displayed by a compound or molecule which has potential physiologic, pharmacologic, diagnostic, or therapeutic applications.

Carbohydrate receptor: Any molecule that binds any carbohydrate. Typically the molecule is a macromolecule such as a protein or DNA.

Glycoconjugate: Any compound or molecule that is covalently bound to a glycosidic residue.

Glycoside: Any sugar containing at least one pentose or hexose residue in which the anomeric carbon bears a non-hydrogen substituent. Typically, the non-hydrogen substituent is a heteroatom, such as nitrogen, oxygen, phosphorus, silicon or sulfur.

Glycosyl acceptor: Any compound that contains at least one nucleophilic group which, under the conditions of the single-step process of the present invention, is able to form a covalent bond with the anomeric carbon of a glycosyl donor. As referred to herein, a glycosyl acceptor is any sugar or glycoconjugate that contains unprotected hydroxyl, amino, or mercapto groups or such groups that are blocked by protecting groups that can be removed in situ, i.e., under the conditions of the single-step process of the present invention.

Glycosyl donor: A sugar or glycosidic residue that bears a sulfoxide group at the anomeric carbon, which group on activation renders the anomeric carbon susceptible to attack by the nucleophilic group of a glycosyl acceptor to form the glycosidic linkage.

Glycosidic libraries: A mixture of oligosaccharides of varying sequences which can be subjected to a screening procedure to identify compounds or molecules that exhibit biological activity. Such libraries may also include various glycoconjugates.

Monofunctional glycosyl acceptor: A glycosyl acceptor as in the definition above, with the additional provision that the capacity to act as a glycosyl donor at the same time (i.e., under the conditions of the single step process of the present invention) is specifically excluded.

Monofunctional glycosyl donor: A glycosyl donor as in the definition above, with the additional provision that the capacity to act as a glycosyl acceptor at the same time (i.e., under the conditions of the single step process of the present invention) is specifically excluded.

Monofunctional glycosyl unit: A sugar that is either a glycosyl acceptor or a glycosyl donor but does not have the capacity to function as both upon activation under the conditions of the single step process of the present invention.

Oligosaccharides: A glycosidic residue having three or more monosaccharide units joined by glycglycosidic linkages.

Potential glycosyl acceptor: Any compound containing at least one nucleophilic group which is potentially able to form a covalent bond with the anomeric carbon of a glycosyl donor.

Single step reaction: A single step reaction is defined as a chemical transformation or set of transformations carried out in a "single" reaction vessel without the need for intermediate isolation or purification steps (i.e., a one-step or one-pot reaction).

Temporal protecting group: A blocking or protecting group that can be removed in situ, preferably, but not necessarily, under the same conditions used to activate an anomeric sulfoxide group.

5.2. General Methods

The following general methods have been divided into two main categories: the first concerns solution reactions involving the formation of multiple glycosidic bonds and the second relates to the synthesis of oligosaccharides in which the growing oligomer is bound to a solid support.

5.2.1. Formation Of Multiple Glycosidic Linkages In Solution

One or more glycosyl donors having alkyl or aryl sulfoxides at the anomeric position and one or more glycosyl acceptors having one or more free hydroxyls and/or other nucleophilic groups (e.g., amines) and/or silyl ether protected hydroxyls are combined in a reaction vessel. The resulting mixture may include both monofunctional glycosyl donors and glycosyl acceptors as well as bifunctional glycosyl units, i.e., saccharides that can function simultaneously as glycosyl donors and acceptors. However, in order to form more than one glycosidic linkage (i.e., to produce a trisaccharide or longer product), at least one of the reactants must be a bifunctional glycosyl unit.

The glycosyl acceptors and donors may be blocked by a suitable protecting group, including, but not limited to, ether, ester, acetamido, or thioester protecting groups, at one or more positions. However, it is understood that an ester (or acetamido or thioester) protecting group at C-2 of a glycosyl donor will influence the stereochemical outcome of glycosylation, resulting in a 1,2-trans glycosidic bond.

The mixture of glycosyl donors and acceptors is dissolved under anhydrous conditions in a non-nucleophilic solvent, including, but not limited to, toluene, ether, tetrahydrofuran (THF), methylene chloride, chloroform, propionitrile, or mixtures thereof. It has been found that the choice of solvent influences the stereochemical outcome of glycosylation for reactions in which neighboring group participation is not involved. In general, for a given donor/acceptor pair, the use of a non-polar solvent, such as toluene, results in the formation of a higher percentage of alpha isomer, while the use of a more polar solvent, such as propionitrile, results in formation of a higher percentage of the beta anomer.

The reaction is initiated by the addition of an effective amount of an activating agent. In a particular embodiment of the present invention, 0.5 equiv. of triflic anhydride, plus 1.5 equiv. base (as an acid scavenger), are added to the reaction mixture. (Equivalents are relative to glycosyl sulfoxide.) A catalytic amount of triflic acid (e.g., <0.05 equiv.) can also be used, preferably along with excess sulfenic acid scavenger (e.g., ca. 20 equiv. of methyl propiolate). It has been found that catalytic triflic acid is preferred when the reaction mixture contains 2-deoxy glycosyl donors or when one of the glycosyl acceptors in the reaction is a silyl ether. On the other hand, triflic anhydride is preferred when maximum reactivity of the glycosyl donors is important. However, it should be noted that the moderately basic conditions that obtain with the use of triflic anhydride are not effective to deprotect certain silyl ethers (e.g., t-butylsilyl ethers). Moreover, although the use of triflic anhydride plus 2,6-ditert-butyl-4-methyl pyridine will result in the in situ deprotection of trimethylsilyl ethers, the use of triflic anhydride plus a stronger base (such as Hunig's base) will not. Thus, both activating agents can be used in reactions involving a bifunctional glycosyl unit containing a silyl ether protected hydroxyl, although triflic anhydride only works under a specific set of conditions (choice of base, choice of silyl protecting group). Otherwise, the two activation methods are usually interchangeable.

The methyl propiolate or other sulfenic acid scavenger and/or activated molecular sieves may be added to the reaction either before or just after the addition of activating agent. Sulfenic acid scavengers significantly improve the yield of glycosylation when catalytic triflic acid is used as the activating agent.

The reaction is normally carried out at low temperature (preferably in the range of about −78° C. to as low as bout −100° C.) but may be allowed to proceed at higher temperatures, in some cases as warm as room temperature.

The reaction is quenched by the addition of aqueous bicarbonate and extracted. The reaction mixture may then be subjected to a purification procedure and/or the product(s) deprotected if necessary. The procedure may be used to construct specific oligosaccharides or mixtures of various oligosaccharides or other glycoconjugates for screening for biological activity.

In particular embodiments of the present invention, it has been discovered that the reactivity of different glycosyl donors may be modulated by manipulating the chemical structure and electronic nature of the anomeric sulfoxide. Such manipulation is due, in part, to the finding that the rate-limiting step in the glycosylation reaction is activation of the sulfoxide by the action of the activating agent. It was subsequently shown that the reactivity of the glycosyl sulfoxides can be influenced by manipulating the nucleophilicity of the sulfoxide oxygen.

Generally, the more nucleophilic the sulfoxide oxygen, the faster the glycosylation reaction. Thus, electron-donating substituents on the R' group attached to the sulfoxide increase the nucleophilicity of the sulfoxide oxygen and speed up the rate of the reaction. By contrast, electron-withdrawing groups decrease the nucleophilicity of the sulfoxide oxygen and slow down the reaction. For example, perbenzylated glucosyl p-methoxyphenyl sulfoxide reacts faster than the corresponding unsubstituted phenyl sulfoxide, while perbenzylated glucosyl p-nitrophenyl sulfoxide reacts slower than the corresponding unsubsituted phenyl sulfoxide.

The ability to influence the nucleophilicity of different sulfoxides and hence to manipulate the reactivity of different glycosyl donors has been exploited in particular embodiments of the present invention. For example, this ability permits sequential glycosylations to take place in solution, as illustrated in FIG. 1.

In yet other embodiments of the present invention, multiple glycosidic linkages are formed in solution using silylated glycosyl acceptors. Silyl ethers are excellent glycosyl acceptors when catalytic triflic acid is the activating agent and trimethylsilyl ethers work well as glycosyl acceptors when triflic anhydride is the activating agent and 2,6-ditertbutyl-4-methyl-pyridine is the base. However, they must be unmasked in order to couple. (Hence the requirement for slightly acidic conditions in the glycosylation reaction when silyl ethers are used as glycosyl acceptors.) Because silyl ethers must be unmasked in order to couple, they react more slowly than unprotected alcohols. In this manner, it has been demonstrated that one can modulate the reactivity of two otherwise similar glycosyl acceptors by selective use of silyl protecting groups.

In selected embodiments of the present invention, the distribution of the length of the oligosaccharides or the glycosidic residues of the glycoconjugates produced can be influenced by varying the ratio of monofunctional glycosyl acceptors and monofunctional glycosyl donors to bifunctional glycosyl units in the reaction mixture. For example, it has been shown that higher ratios of monofunctional glycosyl acceptors to bifunctional glycosyl units in the reaction mixture lead to shorter length polymers. The total concentration of reactants also influences the length distribution. (See, Sections 6.2 and 6.3 and FIGS. 2 and 3, below.)

In particular embodiments of the present invention, it may be desirable to include only two or three different types of sugars in the reaction mixture and to manipulate the reactivity of the glycosyl donors and acceptors so that a specific oligosaccharide is produced. An example of this procedure is given in Sections 6.1. and 6.2, below.

Yet in other embodiments of the present invention, it may be desirable to include several different types of sugars in the reaction mixture in order to generate a chemically diverse mixture of oligosaccharides or glycoconjugate products for the creation of libraries that may be screened for biological activity. An example of such a method is illustrated in Section 6.2 and FIG. 3, below.

The chemical diversity can be influenced by manipulation of the number of different sugars included in the mixture. The chemical diversity will also be a function of the order in which different glycosyl donor/acceptor pairs react. The order in which different donor/acceptor pairs react will depend, in turn, on the relative reactivity of different donor/acceptor pairs. The relative reactivity of different/donor acceptor pairs can be manipulated in various ways, as already described above (e.g., by manipulating the structure of the sulfoxide groups used and by protecting some glycosyl acceptors with silyl ethers to slow down the rate at which they react).

Other factors that influence the relative reactivity of glycosyl donors and acceptors, such as the presence of electronegative protecting groups on the sugar rings or the presence of steric hindrance can also be exploited. (See, e.g., Binkley, R. W. in *Modern Carbohydrate Chemistry*, Marcel Dekker, Inc: New York, 1988; also H. Paulsen, *Angew. Chem. Int. Ed. Engl.* 1982, 22, 156.) Hence, potentially many factors can be taken into account in the implementation of the disclosed method of forming multiple glycosidic linkages to produce chemically diverse mixtures.

5.2.2. Formation Of Glycosidic Linkages On The Solid Phase

A potential glycosyl acceptor is attached to an insoluble support (hereafter termed the resin) through a linkage that can be readily cleaved at the end of the synthesis using conditions that do not damage glycosidic linkages. The resin may be any insoluble polymer that swells in organic solvents and has sites for attaching the glycosyl acceptor. Preferred resins include, but are not limited to, polystyrene resins, such as the Merrifield resin, and PEG-derivatized polystyrene resins, such as the TentaGell resins.

The type of linkage depends on the type of functional sites available on the polymer phase and on the glycosyl acceptor. Because polystyrene-based resins can be readily functionalized with chloromethyl subsitituents, the linkage is typically a benzyl ether, formed by nucleophilic displacement of a benzyl chloride on the resin with a free hydroxyl on the glycosyl acceptor. Alternatively, a benzyl ester can be used which is formed by nucleophilic displacement of a benzyl chloride on the resin with the salt of an acid on the glycosyl acceptor. (FIG. 4) Both types of linkages can be readily hydrolyzed at the anomeric carbon of the glycosyl acceptor by treating the resin with Hg(II) compound. Alternatively, the ester linkage can be hydrolyzed by methanolysis as is done for ester linkages to resins in peptide synthesis. The Hg(II) method is preferred for treating aliquots of the resin to monitor the extent of reaction. The Hg(II) method is also preferred when the lactol of the completed oligosaccharide is desired as a final product. The methanolysis method is preferred when the sulfide of the completed oligosaccharide is desired as a final product (FIG. 4).

The potential glycosyl acceptor may be any molecule having one or more potentially reactive nucleophiles, including potentially reactive hydroxyls, amines, and/or thiols, provided that it also has a suitable site for attachment to the resin. A potentially reactive nucleophile is a free nucleophile or a nucleophile with a temporal protecting group that can be removed readily once the glycosyl acceptor is attached to the resin. The potential glycosyl acceptor may also have permanently protected nucleophiles, which are nucleophiles that cannot be deprotected under the conditions that are used to remove the temporal protecting groups. The potential glycosyl acceptor may be a sugar or some other nucleophile-bearing molecule, including, but not limited to, steroids, amino acids or peptides, polar lipids, polycyclic aromatic compounds, and the like. Protecting group schemes for sugars that permit selective protection and deprotection at any position are well known (See, e.g., Binkley, above).

Following attachment to the resin, the potentially reactive nucleophile is selectively deprotected, if necessary, and the derivatized resin is lyophilized overnight and stored in a desiccator until use. The resin is then preferably placed in a specially designed reactor vessel with a glass frit. Any openings are sealed, e.g., with rubber septa (See, e.g., FIG. 5). There may be many variations on the general apparatus. However, the important features can be enumarted as follows:

a) An inlet for the addition of solvent and dissolved reagents to the reaction chamber and which is suitable for maintaining an anhydrous atmosphere; (In the apparatus shown, a rubber septum over a cup-shaped opening permits the addition of solvent and dissolved reagents by canula or syringe needle while preventing exposure of the reaction chamber to the outside air. In a preferred embodiment of the reaction vessel, this inlet is also equipped with a T-connector or similar adapter which allows the inlet to double as a vent for releasing inert gas, such as nitrogen or argon, to prevent the build up of excess pressure within the apparatus.)

b) A reaction chamber for holding the resin and reagent solution which is equipped with a frit or filter of such coarseness or porosity so that unbound components, such as unreacted dissolved reagents, but not resin, can be washed from the reaction chamber;

c) A port, located on the side of the frit which is opposite to the inlet side, for introduction of an inert gas; the gas passes through the frit, thus agitating the reaction mixture, and settles over the reaction mixture, thus maintaining an anhydrous atmosphere inside the reaction chamber. (As evident from FIG. 5, the argon or nitrogen passes through the resin from below, opposing the flow of solvent through the frit and agitating the resin simultaneously. In a preferred embodiment, this port is equipped with a T-connector or similar adapter to allow the port to be attached to an aspirator for removal of solvent under vacuum.)

Figure 5A:
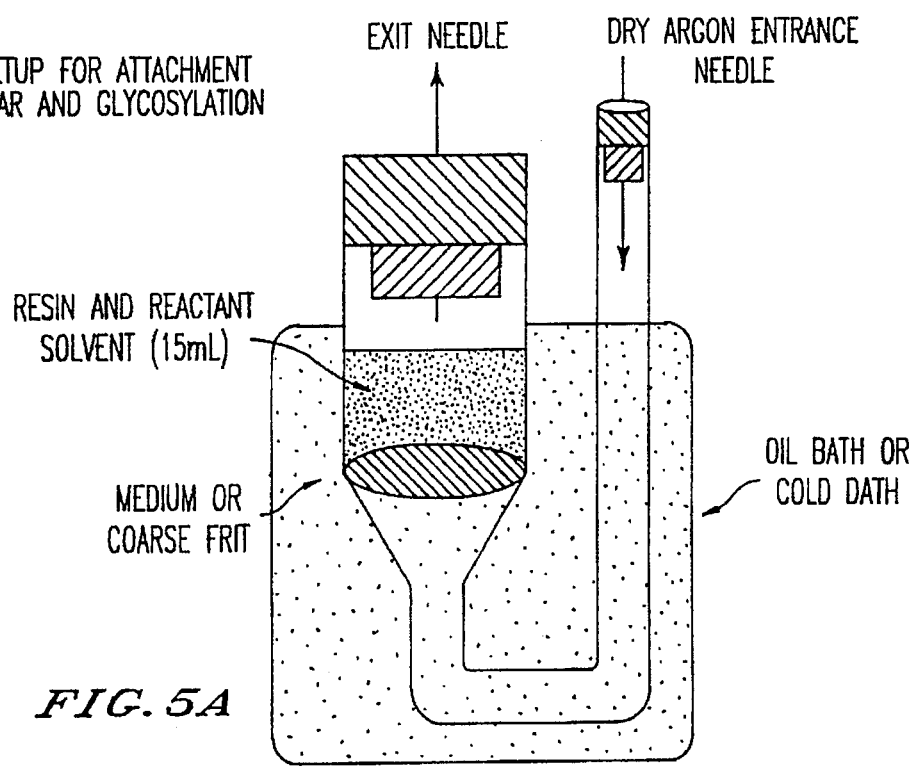
FIG. 5 illustrates an apparatus used to carry out solid phase oligosaccharide synthesis.
Figure 5B:
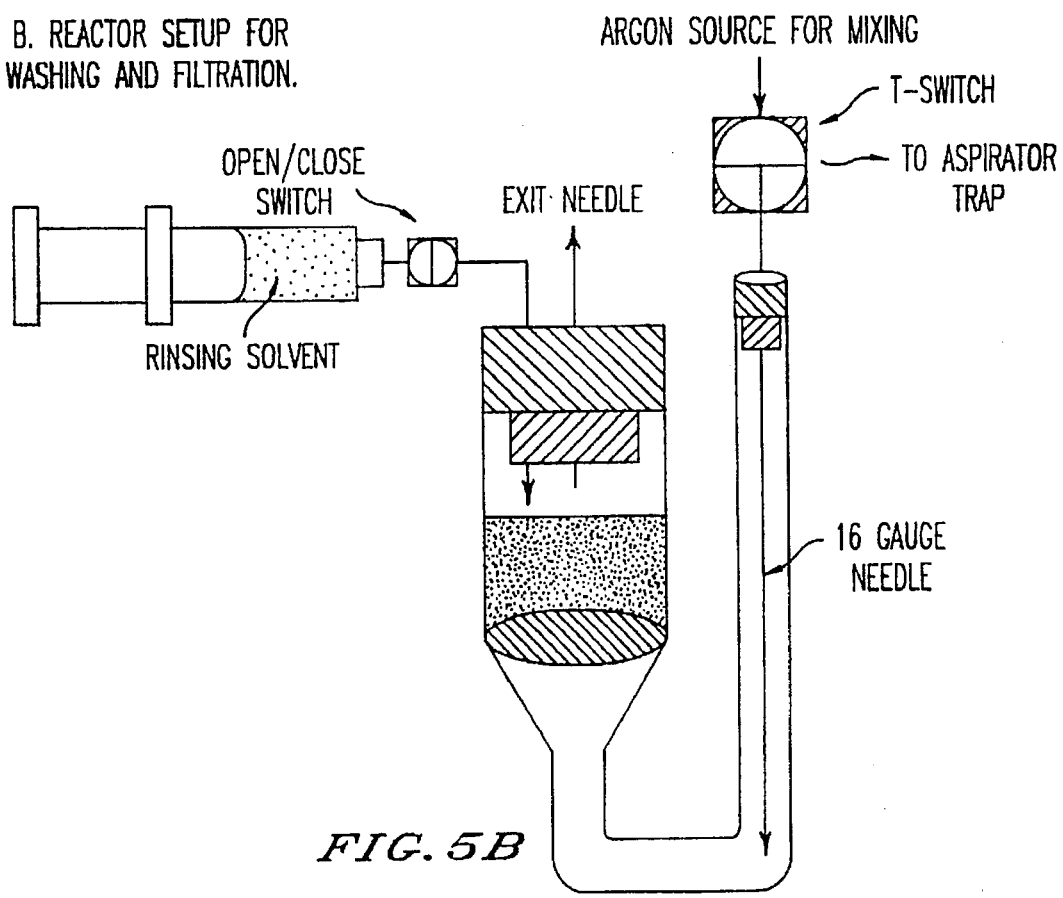

It should also be noted that the configuration of the apparatus is such that the apparatus up to the level of most of the reaction chamber can be immersed in a cooling bath. Hence, below the frit, the apparatus may be in a U-shape, as shown in FIG. 5, so that the gas port can be positioned above the cooling medium.

Next, an inert gas, such as argon or nitrogen, preferably argon, is passed through the resin for about 1 hour. The resin is then suspended in 3–5 mL anhydrous solvent including but not limited to toluene, ether, THF, methylene chloride, chloroform, propionitrile, or mixtures thereof). From the discussion in the previous section, it is understood that the choice of solvent will influence the stereochemical outcome of glycosylation for reactions in which neighboring group participation is not involved. The argon flow is adjusted to agitate the resin gently and prevent solvent from draining through the frit.

A glycosyl sulfoxide is then dissolved under anhydrous conditions in 2–4 mL anhydrous solvent and transferred by canula to the reactor vessel containing the resin. The glycosyl sulfoxide may also have protecting groups present elsewhere in the molecule. If the saccharide chain is to be further extended, the glycosyl sulfoxide must also have at least one temporal protecting group. Typically the glycosyl sulfoxide is added in 2–4-fold excess relative to the amount of glycosyl acceptor on the resin.

Depending on the activation method used to initiate the glycosylation reaction, a non-nucleophilic base, such as 2,6-di-t-butyl-4-methyl pyridine or Hunig's base (diisopropyl ethylamine), may be dissolved with the glycosyl sulfoxide or added to the vessel containing the resin. When used, the base is preferably present in a slight excess relative to the amount of glycosyl sulfoxide added.

The reactor vessel containing the resin is then immersed in a cold bath at $-78°$ C. To activate the glycosyl donors for reaction, either 0.05 equiv. (i.e., catalytic) triflic acid or 0.5 equiv. of triflic anhydride diluted in a large volume of anhydrous solvent is added to the reaction mixture under anhydrous conditions. The molar equivalents are measured relative to the amount of glycosyl sulfoxide used. Also, dilution in a large volume means that the volume of the neat activating agent is diluted at least 100-fold by the addition of the appropriate volume of solvent (e.g., 1 µL of neat activating agent is added to at least 99 µL of solvent before addition to the donor).

The addition of activating agent may be carried out, for example, with the aid of a canula. Other activating agents suitable in the present method include, but are not limited to, an alkyl- or arylsilyl triflate (e.g., trimethylsilyl triflate), an alkyl- or arylsulfenyl triflate, and an alkyl- or arylselenenyl triflate. If protons are generated in the reaction (as when 0.5 equiv. of triflic anhydride is used to activate the sulfoxide), an acid scavenger must be present in the resin mixture. Moreover, unless the activating agent is used in catalytic amounts (e.g., <0.1 equiv relative to glycosyl sulfoxide), the activating agent must be diluted about 100-fold or more prior to addition. It has been discovered with triflic anhydride that dilution is critical, triflation of the glycosyl acceptors on the resin thus being avoided.

Next, the resin is gently agitated by the flow of argon. Typically the reaction is allowed to continue for approximately 30 minutes after which the resin is rinsed repeatedly to remove byproducts and unreacted glycosyl donor. If desired, the reaction may be monitored by removing aliquots of resin, rinsing the resin to remove reagents, and then hydrolyzing the linkage to the resin. Alternatively, if the glycosyl acceptor is a sugar which is attached to the resin via a sulfide derivative linked to the anomeric carbon, the link to the anomeric carbon may be hydrolyzed with a Hg(II) compound. Hydrolysis by Hg(II) is preferred for monitoring the extent of the glycosylation reaction.

The products and the progress of the reaction may be analyzed by thin layer chromatography using standards for comparison. For example, after Hg(II) hydrolysis of an aliquot from the reaction mixture, the soluble products are analyzed by TLC. The absence of the monosaccharide residue that was bound to the resin is taken as an indication that the reaction has proceeded to completion.

To obtain the products, the resin is typically rinsed repeatedly with methylene chloride followed by methanol (preferably, about 10 cycles). The coupling may be repeated if necessary to drive the reaction to completion. Otherwise, if the saccharide chain is to be further extended, temporal protecting groups are next removed, the resin rinsed repeatedly to remove reagents, and another glycosyl sulfoxide residue added as before.

Upon completion of the synthesis and rinsing to remove reagents, the disaccharide, oligosaccharide or glycoconjugate is removed from the resin. The product may then be purified and/or deprotected if desired. Alternatively, the disaccharide, oligosaccharide or glycoconjugate may be used while still attached to the resin in screening procedures to elucidate biological activity.

Strategically, mixtures of oligosaccharides can also be produced by solid phase synthesis and screened for biological activity. To produce mixtures, more than one different type of glycosyl sulfoxide is added to the resin at one or more cycles of the synthesis. It may be desirable to vary the sugars at only one position in the synthesis to probe the structural requirements at that position. In this way, structure-activity relationships can be rapidly evaluated in cases where both a particular carbohydrate and its receptor are known. Alternatively, it may be desirable to vary the sugars at several positions in the synthesis, producing a complex mixture that can be screened for binding to various receptors. In either case, if activity is detected, the active compound(s) can be identified using methods similar to those used in the peptide field for identifying active peptides from mixtures produced by solid phase synthesis. (See, for example, Furka et al. Int. *J. Peptide Protein Res.* 1992, 37, 487; Lam et al. *Nature* 1991, 354, 82; Houghten, R. A. *Nature* 1991, 354, 84; Zuckermann, R. N. et al. *Proc. Natl. Acad. Sci. USA* 1992, 89, 4505. Petithory, J. R. *Proc. Natl. Acad. Sci. USA*, 1991, 88, 11510. Geyse, H. M. et al. *Proc. Natl. Acad. Sci. USA*, 1984, 81, 3998. Houghten, R. A.; *Proc. Natl. Acad. Sci. USA*, 1985, 82, 5131; Fodor et al. *Science* 1991, 251, 767.)

6. EXAMPLES

The following specific examples are provided to better assist the reader in the various aspects of practicing the present invention. As these specific examples are merely illustrative, nothing in the following descriptions should be construed as limiting the invention in any way. Such limitations are, of course, defined solely by the accompanying claims.

6.1. Synthesis Of The Ciclamycin 0 Trisaccharide In A Single Step

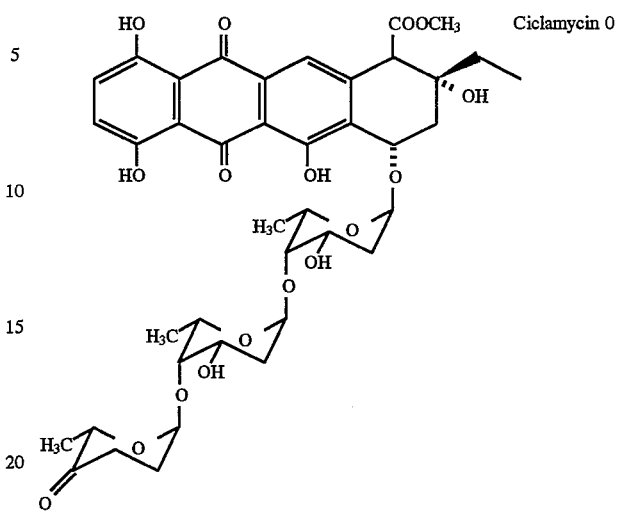

FIG. 1 illustrates one embodiment of the process for forming multiple glycosidic linkages in solution in which a specific trisaccharide, the ciclamycin 0 trisaccharide, is synthesized stereospecifically in protected form in a single step from the component monosaccharides. The monosaccharides 1, 2, and 3 are combined in a ratio of 3:2:1, as shown (417 mg, 1.812 mmol; 541 mg, 1.2 mmol; and 165 mg, 0.604 mmol, respectively). Water is then removed from the mixture by distillation of the azeotrope from anhydrous toluene. (This drying step is carried out by dissolving the sugar mixture in toluene (ca. 30 mL) and removing the toluene on a rotary evaporator under vacuum. The anhydrous sugar mixture is then used directly or stored under inert gases until needed.)

The anhydrous sugar mixture is next dissolved in 20 mL of anhydrous methylene chloride in a 50 mL flame dried flask. Then, 20 mL of freshly distilled diethyl ether containing 20 equivalents of methyl propiolate is added. (The propiolate ester is used to scavenge the sulfonic acid that is produced in the reaction.) The solution is then cooled to −78° C. A catalytic amount of triflic acid (5.3 μL, 0.05 eq.) is then added dropwise, and the reaction is allowed to warm from −78° to −70° C. over a period of 45 minutes and then quenched with saturated NaHCO$_3$. The biphasic mixture is then extracted with CH$_2$Cl$_2$ (3×15 mL). The organic extracts are combined, dried over anhydrous Na$_2$SO$_4$ and concentrated. The major product, trisaccharide 5, is isolated in 25% yield, based on monosaccharide 3, after extraction with ethyl acetate and flash chromatography on silica gel (20% ethyl acetate/petroleum ether).

The $^1$H NMR spectra of trisaccharide 5 are shown in FIGS. 12 and 13. The stereoselectivity achieved is a function of the donor-acceptor pairs and the glycosylation conditions (solvent, temperature). We have found that catalytic triflic acid does not anomerize glycosidic linkages at an appreciable rate below −30° C. No other trisaccharide is produced. Indeed, the only other significant coupled product detected from the reaction is disaccharide 4 (Scheme 1 of FIG. 1, 15% yield; $^1$H NMR, FIG. 14), the precursor to the trisaccharide 5. Less than 5% of the disaccharide from the cross coupling of phenyl sulfoxide 1 and free alcohol 3 was detected even though 1 is present in excess; no disaccharide from the cross coupling of 1 and 2 was detected.

Thus, the yield of trisaccharide 5 in the reaction is not limited by any undesired cross coupling. However, the instability of the glycosyl donors, particularly keto sulfoxide 1, which decomposes readily at room temperature even in the absence of activating agent, can affect the yield.

The products of the reaction indicate that glycosylation takes place in a sequential manner, with p-methoxy phenyl sulfoxide 2 activating faster than phenyl sulfoxide 1, and C-4 alcohol 3 reacting faster than C-4 silyl ether 2. Consistent with this sequence, if the reaction is quenched at −100° C., only the silyl ether of disaccharide 4 can be isolated (60%).

Thus, the products of the one step reaction described above illustrate the principle established by the present invention; i.e. that the reactivity of both glycosyl donors and glycosyl acceptors can be manipulated effectively so that glycosylation takes place in a sequential manner to produce a desired oligosaccharide in a single step.

Finally, it should be noted that the trisaccharide (5) produced in the one step reaction has an anomeric phenyl sulfide on the A ring. Anomeric phenyl sulfides are stable ("disarmed") to the conditions that activate anomeric phenyl sulfoxides for glycosylation, but they can be readily oxidized under mild conditions. (See Mootoo, D. R.; Konradsson, P.; Udodong, U.; Fraser-Reid, B. *J. Am. Chem. Soc.* 1988, 110, 5583; Veeneman, G. H.; van Boom, J. H. *Tet. Lett.* 1990, 31 275; and Mehta, S.; Pinto, B. J. *Tet. Lett.* 1991, 32, 4435.) Thus, the sulfoxide glycosylation reaction also lends itself well to an iterative strategy for oligosaccharide synthesis. (See Friesen, R. W.; Danishefsky, S. J. *J. Am. Chem. Soc.* 1989, 111, 6656; Halcomb, R. L.; Danifsky, S. J. *J. Am. Chem. Soc.* 1989, 111, 6661; Mootoo, D. R.; Konradsson, P.; Udodong, U.; Fraser-Reid, B. *J. Am. Chem. Soc.* 1988, 110, 5583; Veeneman, G. H.; van Boom, J. H. *Tet. Lett.* 1990, 31 275; and Mehta, S.; Pinto, B. J. *Tet. Lett.* 1991, 32, 4435; Nicolaou, K. C.; Dolle, R. E.; Papahatjis, D. P.; Randall, J. L. *J. Am. Chem. Soc.* 1984, 106, 4189; Mootoo, D. R.; Konradsson, P.; Fraser-Reid, B. *J. Am. Chem. Soc.* 1989, 111, 8540; Barrett, Anthony G. J.; Bezuidenhoudt, Barend C. B.; Gasiecki, A. F.; Howell, A. R.; Russell, J. A. *J. Am. Chem. Soc.*, 1989, 111, 1392. The ciclamycin trisaccharide 5 is oxidized to the corresponding sulfoxide in 80% yield (1.2 eq. mCPBA, $CH_2Cl_2$. −78° C. to −50° C., 2 hr) and is ready for coupling to the ciclamycin chromophore.

Monosaccharide 1 is prepared from L-rhamnose in 60% overall yield ($^1$H NMR; FIG. 9). (a) Roth, W.; Pigman, W., *Methods in Carbohydrate chemistry* vol II, 405. (b) Martin, A.; Pais, M.; Monneret, C., *Carbohydr. Res.* 1983, 115, 21. (c) Ferrier, R. J.; Furneaux, R. H., *Carbohydr. Res.* 1976, 52, 63. (d) Omura, K.; Swern, D., *Tetrahedron* 1978, 34, 1651. Monosaccharides 2 ($^1$H NMR; FIG. 10) and 3 ($^1$H NMR; FIG. 11) are prepared from L-fucose with overall yields of 47% and 52%, respectively. (a) Giese, B.; Groninger, K. S.; Witzel, T.; Korth, H.-G.; Sustmann, R., *Angew Chem. Int. Ed. Engl.* 1987, 26, 233. (b) 7c. (c) Ogawa, T.; Matsui, M., *Carbohydr. Res.* 1978, 62, C-1.

From the principle established herein, it should be apparent to one of ordinary skill in the art that the ability to manipulate the reactivity of both glycosyl donors and glycosyl acceptors, to control the order in which glycosylation takes place, can be exploited to synthesize many other oligosaccharides or glycoconjugates rapidly, efficiently and in high yield.

6.2. One-Pot Synthesis Of Homopolymers Of Different Lengths

FIG. 2 illustrates another aspect of the present invention which allows the synthesis of "homopolymers" of different lengths. Hence, alpha-linked homopolymers of 2-deoxy fucose with different length distributions are produced by mixing in separate flasks different ratios of the bifunctional sulfoxide 4-methoxy phenyl-3-O-benzyl-4-O-trimethylsilyl-2-deoxy-1-sulfinyl-α-L-fucopyranoside, B, with the monofunctional glycosyl acceptor methyl-3-O-benzyl-2-deoxy-α-L-fucopyranoside, A, and the base 2,6-di-t-butyl-4-methylpyridine (2 equivalents relative to sulfoxide). The Table, below, indicates the reactant ratio that was used for each of the experiments 6.2.1–6.2.5. The mixtures are first dried thoroughly by azeotropic distillation from toluene (preferably, three times, as above).

The mixtures are then each dissolved in 2.5–5 mL anhydrous methylene chloride and added to separate 25 mL flame dried flasks under argon. To each reaction mixture is added an equal volume of freshly distilled diethyl ether. The flasks are next cooled to −78° C. using an acetone/dry ice bath. After 5 minutes, a methylene chloride solution of triflic anhydride (1.0 equiv relative to B) is added dropwise to the reaction mixtures. The reactions are monitored by thin layer chromatography using 15% ethyl acetate/petroleum ether as the eluant.

After warming to −70° C. over a period of about half an hour, the reaction mixtures are quenched with saturated solution of $NaHCO_3$ (approximately 30 mL each). Each of the resulting biphasic mixtures is extracted with methylene chloride (3×15 mL). The organic extracts are combined, dried over anhydrous $Na_2SO_4$ and concentrated. Flash chromatography (1:5 ethyl acetate/petroleum ether) is used to isolate the glycosylated products from each reaction. The length distribution of "homopolymers" produced is found to vary with the ratio of A to B and also with the total concentration of reactants in the reaction mixture, as shown in the Table, below.

TABLE

Relative Amounts Of Various "Homopolymers" Produced As A Function Of Molar Ratios Of Reactant And Total Concentration

| Entry | A:B (ratio) | [A + B] (mmol/mL) | AB (%) | $AB^2$ (%) | $AB^3$ (%) | $AB^4$ (%) | $AB^5$ (%) |
|---|---|---|---|---|---|---|---|
| 6.2.1 | 1:1 | 0.088 | 40 | — | — | — | — |
| 6.2.2 | 1:2 | 0.083 | 45 | 20 | — | — | — |
| 6.2.3 | 1:3 | 0.096 | 60 | 30 | 8.7 | — | — |
| 6.2.4 | 1:5 | 0.050 | 50 | 30 | 8.0 | 1.5 | |
| 6.2.5 | 1:3 | 0.233 | 30 | 40 | 17 | 8.4 | 1.7 |

AB = A—B ($^1$H NMR; FIGS. 15 and 16)
$AB^2$ = A—B—B ($^1$H NMR; FIGS. 17 and 18)
$AB^3$ = A—B—B—B ($^1$H NMR; FIGS. 19 and 20)
$AB^4$ = A—B—B—B—B ($^1$H NMR; FIGS. 21 and 22)
$AB^5$ = A—B—B—B—B—B 6.3. One-Pot Synthesis Of Glycoconjugates With Potential DNA Binding Activity The strategy for forming multiple glycosidic linkages in solution can be used to synthesize in the same reaction several glycoconjugates with potential DNA binding activity. Depending on the situation, the glycoconjugates can be separated and screened individually for DNA binding activity or they can be screened as mixtures. For example, a mixture of glycoconjugates, each comprised of a potential DNA intercalator and an oligosaccharide side chain, and differing one from another only in the length of the oligosaccharide side chain, are synthesized as in Example 6.2, but using a 4:1 ration of bifunctional donor to glycosyl acceptor. Specifically, the 2-deoxy fucosyl sulfoxide derivative B (908 mg, 1.90 mmol), the glycosyl acceptor A (294 mg, 0.48 mmol), and 2,6-ditert-butyl-4-methyl pyridine (779 mg, 3.80 mmol) are combined, dried by azeotrope distillation three times from toluene and then dissolved in 10 mL of a 1:1 mixture of ether/methylene chloride (freshly distilled solvents). The solution is transferred to a flame dried flask under argon. The flask is cooled to −78° C. using an acetone/dry ice bath. After 5 minutes, 161.1 μL (0.96 mmol) triflic anhydride is added dropwise to the reaction mixture. The reaction is slowly warmed to −70° C. over a period of half an hour and then quenched by pouring into a saturated solution of NaHCO$_3$ (30 mL). The mixture is extracted with methylene chloride (3×15 mL). The combined organic extracts are dried over anhydrous Na$_2$SO$_4$, filtered, and the solvent removed under vacuum. The reaction is dissolved in 10 mL of wet methylene chloride and treated with excess diclorodicyanoguinone (DDQ) at room temperature for 1 hour to remove the p-methoxy benzyl ether protecting groups. The solvent is then removed under vacuum and the components are separated by flash chromatrography on silica gel.

Their relative affinities for DNA are evaluated to determine the preferred length of the oligosaccharide side chain. Affinity chromatography can be used to identify oligosaccharides that bind to particular receptors. For example, a mixture of compounds is passed over a column containing a solid support to which is attached a receptor of interest (or ligand, if the mobile phase contains a mixture of potential receptors). Compounds that bind to the receptor are retained on the column longer than compounds that do not. Compounds can be fractionated according to their affinity for the receptor.

Thus, receptors that bind carbohydrates can be attached to the solid support. Carbohydrate receptors may be comprised of DNA (double or single stranded), RNA, protein, oligosaccharides, or other molecules. Methods to attach nucleic acids, proteins, and oligosaccharides to solid supports for use in affinity chromatography have been described. See: (a) *Template Chromatography of Nucleic Acids and Proteins*, Schott, H. Marcel Dekker, Inc.: New York, 1984; (b) *Glycoconjugates: Composition, Structure and Function*, Allen, H. J.; Kisailus, E. C., Eds. Marcel Dekker: New York 1992 (and references therein). (NOTE: Retention times can also be used to quantitate affinities for single compounds passed down the affinity column.)

In another example, glycosyl acceptor A (FIG. 3) is premixed with 2,3-p-methoxy benzyl-4-trimethylsilyl rhamnosyl sulfoxide C (FIG. 3) and allowed to react under conditions (e.g., temperature, solvent, concentration, donor/ acceptor ratio) identical to those described in Example 6.2.5. After workup and removal of the p-methoxy benzyl protecting groups with DDQ, as above, the mixture of glycoconjugates is separated by flash chromatography on silica gel and the relative affinities of the different compounds for DNA are determined. The glycoconjugates produced by the methods described in Examples 6.3.1 and 6.3.2 are compared with respect to their abilities to bind to DNA. In this way, the effects of different sugars on DNA binding affinity can be compared to identify preferred sugars.

Figure 3A:
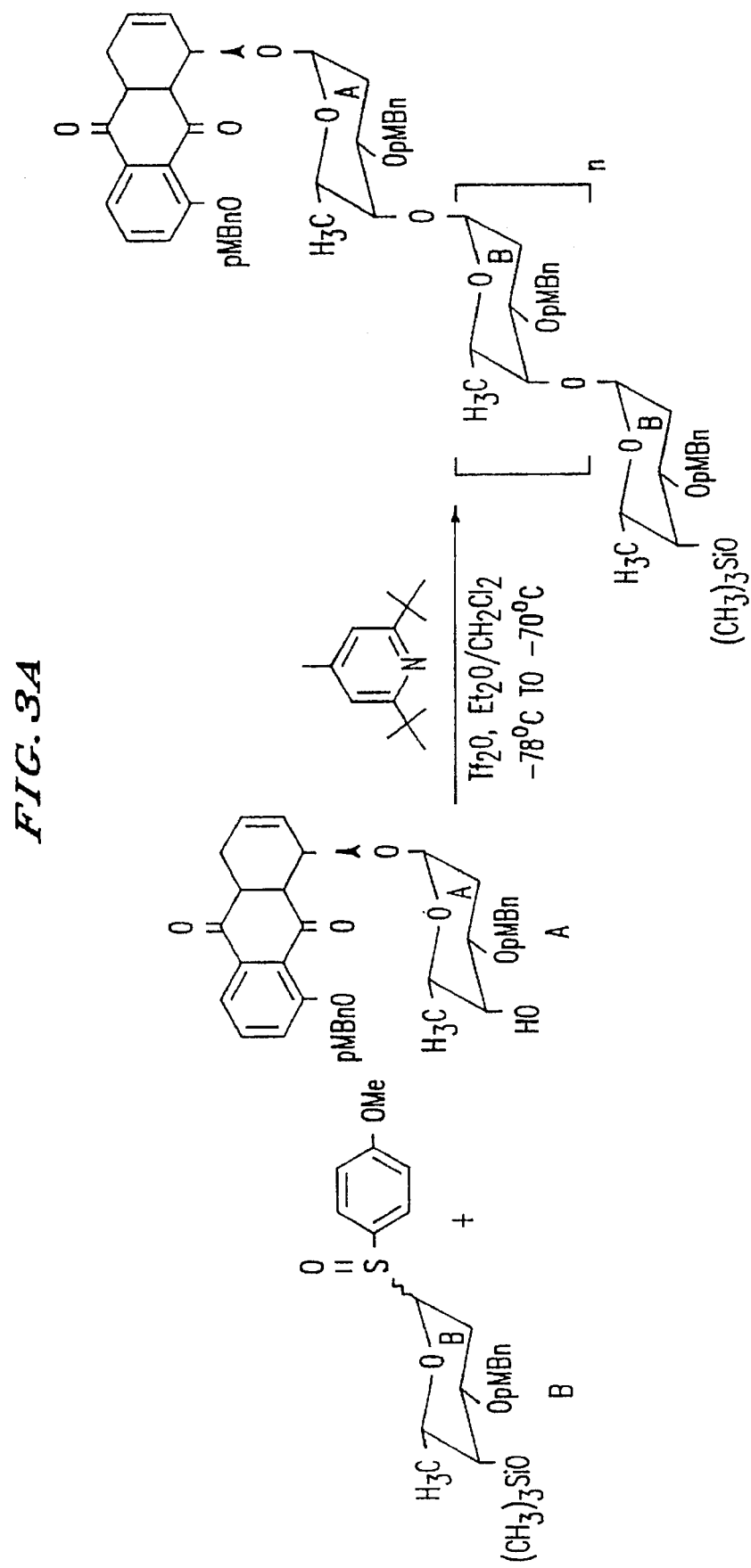
FIG. 3 illustrates a process of synthesizing mixtures of glycoconjugates having biological activity, including potential DNA binding activity. The glycoconjugates so produced can subsequently be screened (e.g., for DNA binding activity) to evaluate the preferred length and the preferred sugar residues of the oligosaccharide portion of the glycoconjugate based on the activity being tested.
Figure 3B:
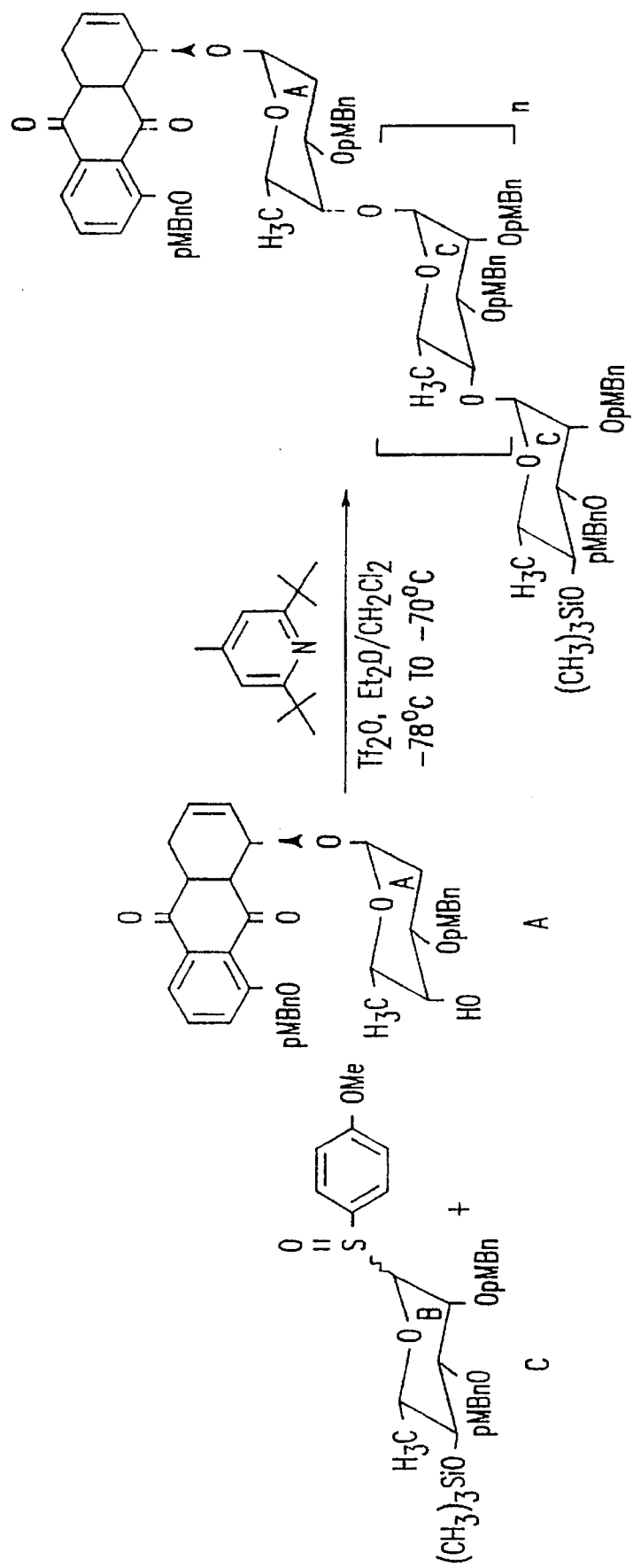
Figure 4A:
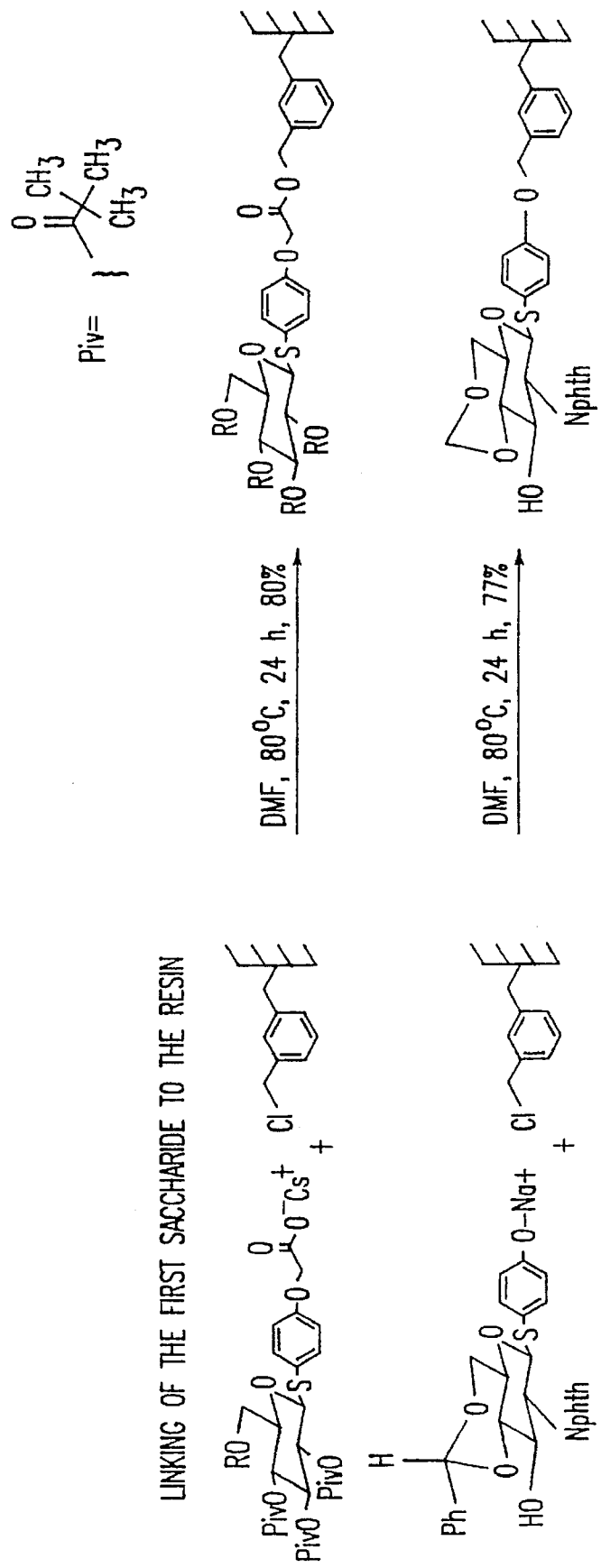
FIG. 4 illustrates methods of forming and removing two exemplary types of linkages from a solid support (e.g., polystyrene resin).
Figure 4B:
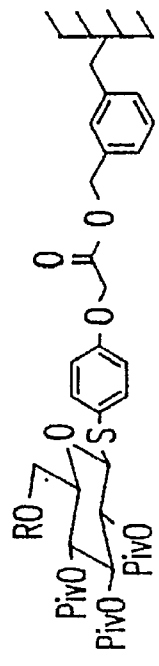
Figure 4B:
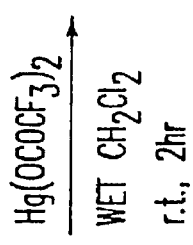
Figure 4B:
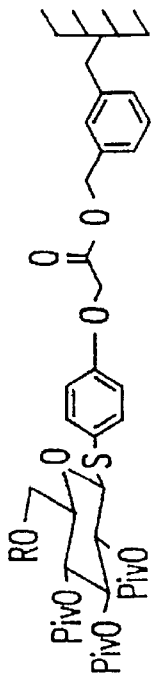
Figure 4B:
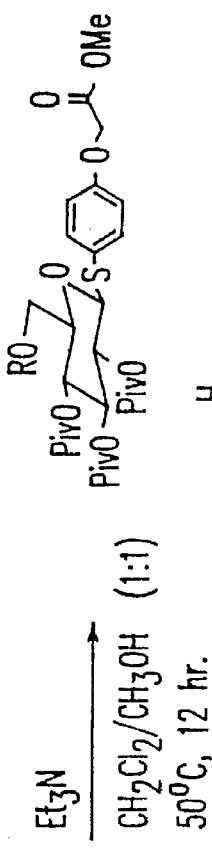
Figure 4B:
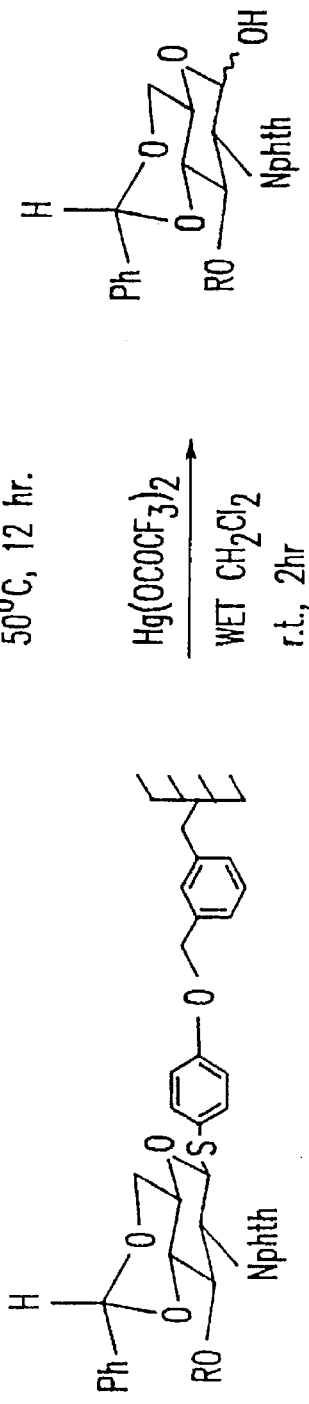

The glycosyl acceptor A in FIG. 3 is made by glycosylating a suitably protected juglone derivative (obtained following the procedures of (a) Inhoffen, H. H.; Muxfeldt, H.; Schaefer, H.; Kramer, H. *Croatica Chem. Acta.* 1957, 29, 329; (b) Trost, B. M.; Ippen, J.; Vladuchick, W. C. *J. Am. Chem. Soc.* 1977, 99, 8116; (c) Stork, G.; Hagedorn, A. A. *J. Am. Chem. Soc.* 1978, 100, 3609) with compound B (FIG. 3) using Tf$_2$O-Hunig's base CH$_2$Cl$_2$/ether (1:1) at low temperature. After a standard workup (including extraction, as described in the other Examples herein) and removal of solvent, the product mixture is dissolved in methylene chloride and treated with excess tetrabutylammonium fluoride at 0° C. The solvent is then removed in vacuo and the product isolated by flash chromatography.

The general process described above may also be applied to the synthesis of mixtures of glycoconjugates containing several different sugars. In this case, two or more bifunctional glycosyl donors are used in the reaction. After deprotection, the resulting mixture of glycoconjugates can be screened for DNA binding activity by passing it down a DNA affinity column. Compounds can be fractionated according to their retention times on the affinity column. Compounds with long retention times can be isolated and identified using standard methods for structure elucidation.

6.4. Synthesis Of A β-Linked Disaccharide On The Solid Phase

To a 10 mL solution of DMF containing 0.338 g (0.350 mmol) of 2,3,4-tribenzyl-6-tritylgalactose-1-p-hydroxy phenythioglycoside cesium acetate (X, FIG. 6) is added 0.356 g (0.385 mmol Cl eguiv, 1,1 equiv) of Merrifield resin (BACHEM Bioscience). This mixture is agitated with a wrist action shaker for 24 h under argon atmosphere at 75° C. At this time, the polymer is poured into a tared coarse-fritted Gooch funnel and washed repeatedly with methanol and methylene chloride. The funnel is then dried for 4 h in a lyophilizer jar at 20 milliTorr. A mass change of 0.244 g is recorded, which is calculated to be 85% chemical yield with respect to the cesium salt.

The polymer in the coarse-fritted Gooch funnel is then treated by vacuum filtration at moderate flow rate with 40 mL of 10% trifluoroacetic acid (TFA) in methylene chloride until no yellow color is apparent in the filtrate. (The TFA is used to remove the trityl protecting groups.) The polymer is next washed repeatedly with methanol and methylene chloride. The funnel, together with the resin-linked nucleophile, is then dried for 4 h in a lyophilizer jar at 20 milliTorr before "massing". A mass change of 0.065 g is subsequently measured, which is calculated to be 83% chemical yield with respect to the cesium salt. The concentration of the resin-linked nucleophile (resin-X, FIG. 6) is then calculated to be 0.544 mmol/g.

200 mg (i.e., 0.11 mmol) of derivatized resin is lyophilized overnight in the reaction vessel and then purged for 1 hour with argon. The resin is then suspended in 5 mL CH$_2$Cl$_2$. 4 equivalents (0.44 mmol) of 2-pivaloyl-3,4-benzyl-6-p-methoxy benzyl galactosyl phenyl sulfoxide (Y, FIG. 6) and 6 equivalents (0.66 mmol) 2,6-di-t-butyl-4-methyl pyridine are dissolved in 5 mL methylene chloride and added by canula to the reactor vessel. The mixture is agitated gently by argon flow for 30 minutes at room temperature and then the reactor vessel is immersed in a cold bath and allowed to cool to −60° C. 2 equivalents (0.22 mmol) of triflic anhydride diluted one hundred fold (v/v) in methylene chloride are added slowly (over 15 minutes) to the reaction vessel. The resulting reaction mixture is gently agitated for 1 hour.

After the reaction is completed, as indicated by the Hg(II) hydrolysis method and TLC analysis, the solvent and unbound reagents are then drained from the reactor vessel, and the resin mixture is rinsed repeatedly with methanol followed by methylene chloride. Subsequently, the resin mixture is suspended in 15 mL of methylene chloride and then treated with excess Hg(OCOCF$_3$)$_2$ for 8 hours to cleave the glycosidic linkage to the resin. (Note: only 5 minutes is required to remove sufficient product from the resin to monitor the reaction by TLC analysis.) The solvent is allowed to drain from the resin. Additional solvent is then used to rinse the resin. The filtrates are then combined, extracted three times with water and concentrated by evaporation. The desired β-linked disaccharide is obtained by flash chromatography on silica gel. No α-linked disaccharide is isolated from the reaction.

Figure 6:
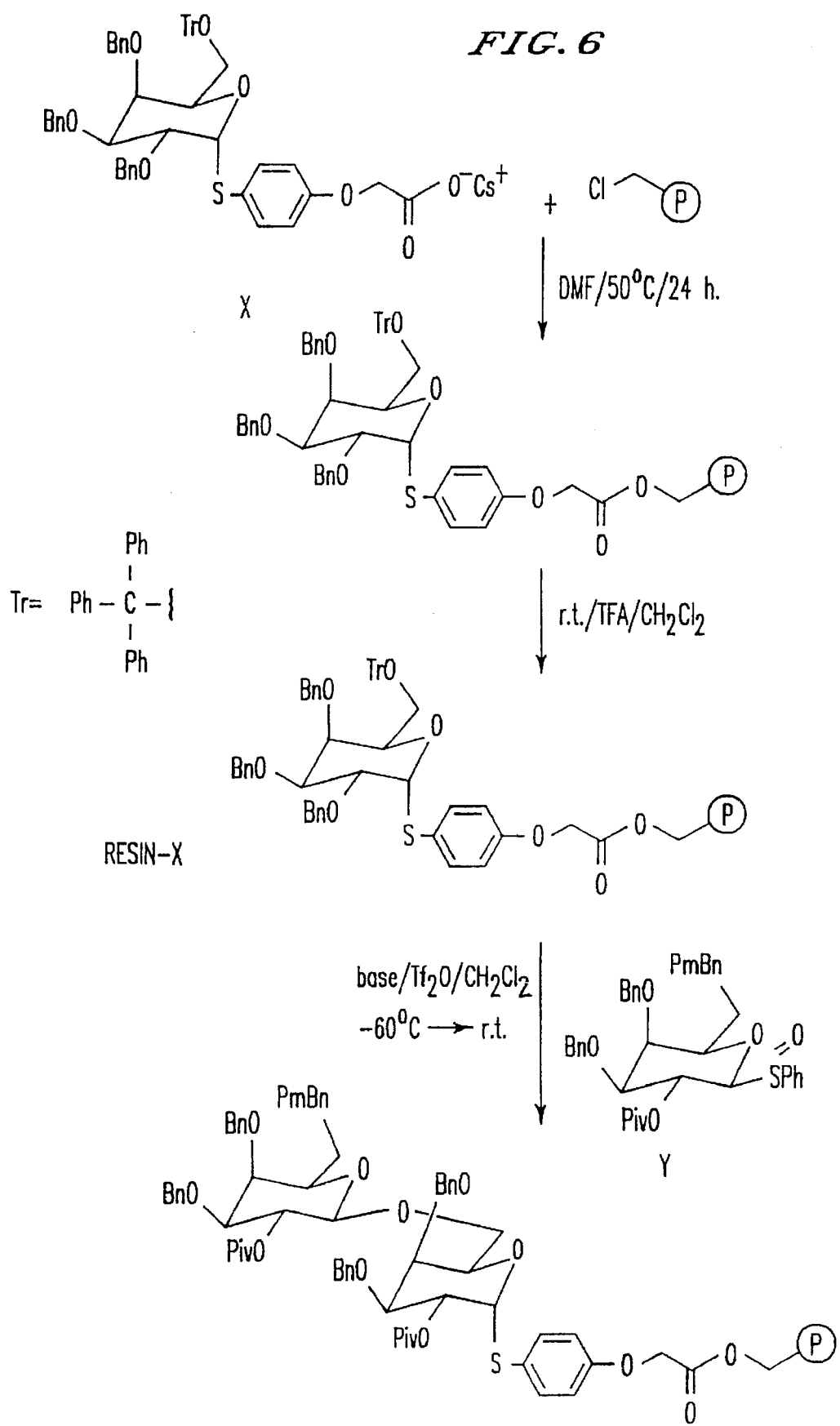
FIG. 6 illustrates the general scheme for synthesis of a β-linked disaccharide on the solid phase.

Thiosugar X in FIG. 6 is prepared from the readily available 1,6-anhydroglucose by treatment with benzyl bromide followed by acidic hydrolysis ($H_2SO_4$-THF-$H_2O$), tritylation (trityl chloride-pyridine) of the more reactive C6 primary alcohol, and treatment of the resulting lactol with disulfide xx and tri-n-butylphosphine (i.e., standard procedure for making thiophenyl glycosides from lactols). The disulfide xx is produced by reacting the disulfide of the readily available 4-hydroxythiophenol with α-bromomethyl acetate.

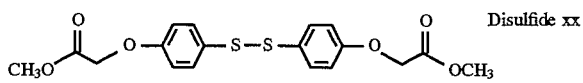

Disulfide xx

Sulfoxide Y in FIG. 6 is prepared from readily available penta-acetylated galactose using the following sequence of reagents: (1) $BF_3$/etherate-ethiophenol; (2) hydroxide; (3) acetone-$H^+$; (4) p-methoxy benzyl bromide-sodium hydride; (5) pivaloyl chloride; (6) mCPBA. Each step is well known in the art and the reactions are carried out under the standard conditions. (See, list of "Standard References" below in Section 6.6.).

The disaccharide produced from the reaction of X and Y is subjected to methanolysis (to remove it from the resin) and is characterized by $^1$H NMR spectroscope. The relevant data include: ($CDCl_3$) 5.58 ppm (d, J=5.3 Hz, H1 of thiosugar), 5.47 ppm (dd, J=7.9, 10.2 Hz, H2 of C2 pivaloylated sugar), 4.45 ppm (d, partially overlapped, H1 of C2 pivaloylated sugar).

6.5. Synthesis Of An α-Linked Disaccharide On The Solid Phase

The sodium salt of a glycosyl acceptor (X, FIG. 7) is attached to the Merrifield resin by the standard method (DMF, 80° C., 24 h). Following the coupling and rinsing (as described in Example 6.4), the resin is lyophilized and weighed. Loading is calculated at 0.52 mmol/g from the mass gain.

200 mg (i.e., 0.1 mmol) of derivatized resin is lyophilized overnight in the reaction vessel (FIG. 7) and then purged for 1 hour with argon. The resin is then suspended in 5 mL methylene chloride. 4 equivalents (0.4 mmol) of perbenzylated fucosyl sulfoxide Y and 6 equivalents of 2,6-di-t-butyl-4-methyl pyridine are dissolved in 5 mL methylene chloride and added by syringe to the reactor vessel. The mixture is agitated gently by argon flow for 30 minutes at room temperature and then the reactor vessel is immersed in a cold bath and allowed to cool to −60° C. 2 equivalents (0.22 mmol) of triflic anhydride diluted one hundred fold in methylene chloride are added slowly by syringe (over 15 minutes) to the reaction vessel. The reaction is gently agitated for 1 hour. The solvent and unbound reagents are then drained from the reactor vessel, and the resin mixture is rinsed repeatedly with methanol followed by methylene chloride. Subsequently the resin mixture is suspended in 15 mL of methylene chloride and then treated with excess $Hg(OCOCF_3)_2$ for 8 hours to cleave the glycosidic linkage to the resin (only 5 minutes is required to remove sufficient product from the resin to monitor the reaction by TLC analysis). The solvent is allowed to drain from the resin as before. The resin is then rinsed with additional solvent and the filtrates combined, extracted three times with water, and concentrated by evaporation. Flash chromatography on silica gel gives only the desired α-linked disaccharide.

Figure 7:
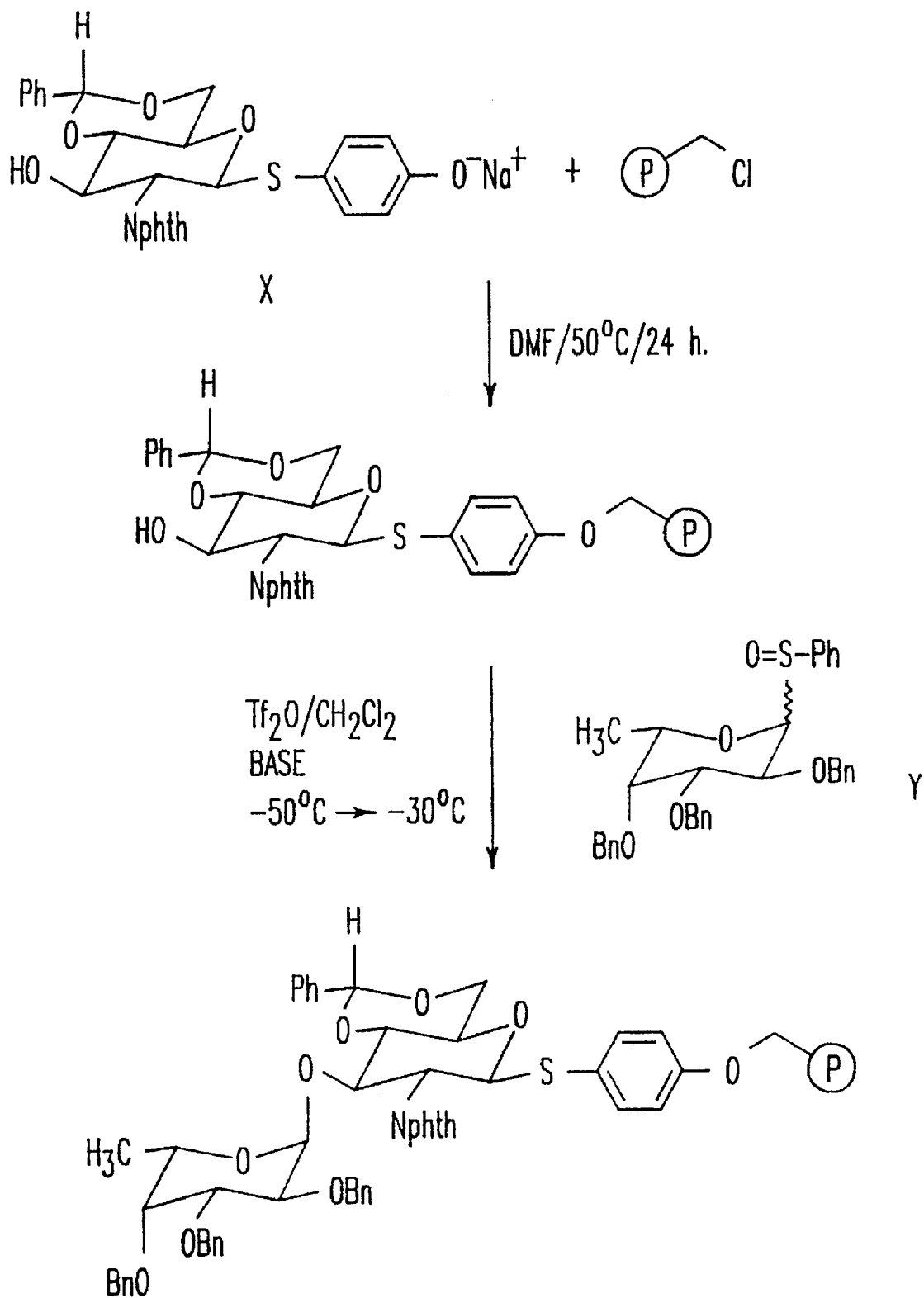
FIG. 7 illustrates the general scheme for synthesis of an α-linked disaccharide on the solid phase.

Thiosugar X in FIG. 7 was prepared from the readily available corresponding glucosamine by treatment with the following reagents: (1) phthalic anhydride; (2) acetic anhydride; (3) tetrachlorotin-4-hydroxy thiophenol; (4) hydroxide; (5) benzaldehyde-$H^+$; (6) NaH, under conditions that are standard in the art. (See, Section 6.6, below).

Sulfoxide Y in FIG. 7 is made from peracetylated fucose by treating the starting material sequentially with $BF_3$/etherate-thiophenol, followed by hydroxide, followed by benzyl bromide, and then with mCPBA. All these steps are standard and well known in the art.

The disaccharide produced from the reaction of X and Y following treatment with $Hg(OCOCF_3)_2$ (to remove it from the resin) is characterized by $^1$H NMR. Relevant data: $CDCl_3$) 5.6 ppm (apparent t, J=7.6 Hz, H1 of C2 phthalimido sugar), 3.35 ppm (d, J=7.6 Hz, lactol OH, i.e., of phthalimido sugar after hydrolytic removal from resin w/Hg (I)I), 4.9 ppm (d, J=2.8 Hz, H1 of fucose derivative).

6.6. Solid Phase Synthesis Of Lewis X Trisaccharide

The sodium salt of a glycosyl acceptor (X, FIG. 8) is attached to the Merrifield resin using the standard method (DMF, 80° C., 24 h). After using the general linking procedure described in detail in Example 6.4, the anhydrous resin is suspended in 5 mL methylene chloride. 4 eq. 2,3,4,6-pivaloylated galactosyl sulfoxide Y and 6 eq. base (as above) is dissolved in 5 mL methylene chloride. The reagent solution is then added to the resin, and the reaction mixture is cooled to −60° C. 2 equivalents of triflic anhydride diluted one hundred fold (v/v) in methylene chloride are then added.

After 30 minutes, the resin is "drained" and rinsed repeatedly with methylene chloride and methanol. The resin is then suspended in 5 mL methylene chloride and cooled to 0° C. 5 mL of a 1:2 solution of trifluoroacetic acid/methylene chloride is then added, and the resin is agitated gently for 5 hours. The resin is then "drained" and rinsed repeatedly with methylene chloride and methanol. Following a final rinse with anhydrous methylene chloride, the resin is suspended in 5 mL of anhydrous methylene chloride. 4 equivalents of 2,3,4-triethylsilyl fucosyl sulfoxide Z and 6 equivalents of hindered base (i.e., that used above) are dissolved in 5 mL methylene chloride and added to the resin. The reaction mixture is cooled to −60° C. 2 equivalents of triflic anhydride are diluted 100 fold in methylene chloride and added slowly by syringe to the reaction. After agitating gently for 30 minutes, the resin is "drained" and rinsed. The trisaccharide is then removed and isolated from the resin using $Hg(OCOCF_3)_2$, as described above in Example 6.4.

Figure 8:
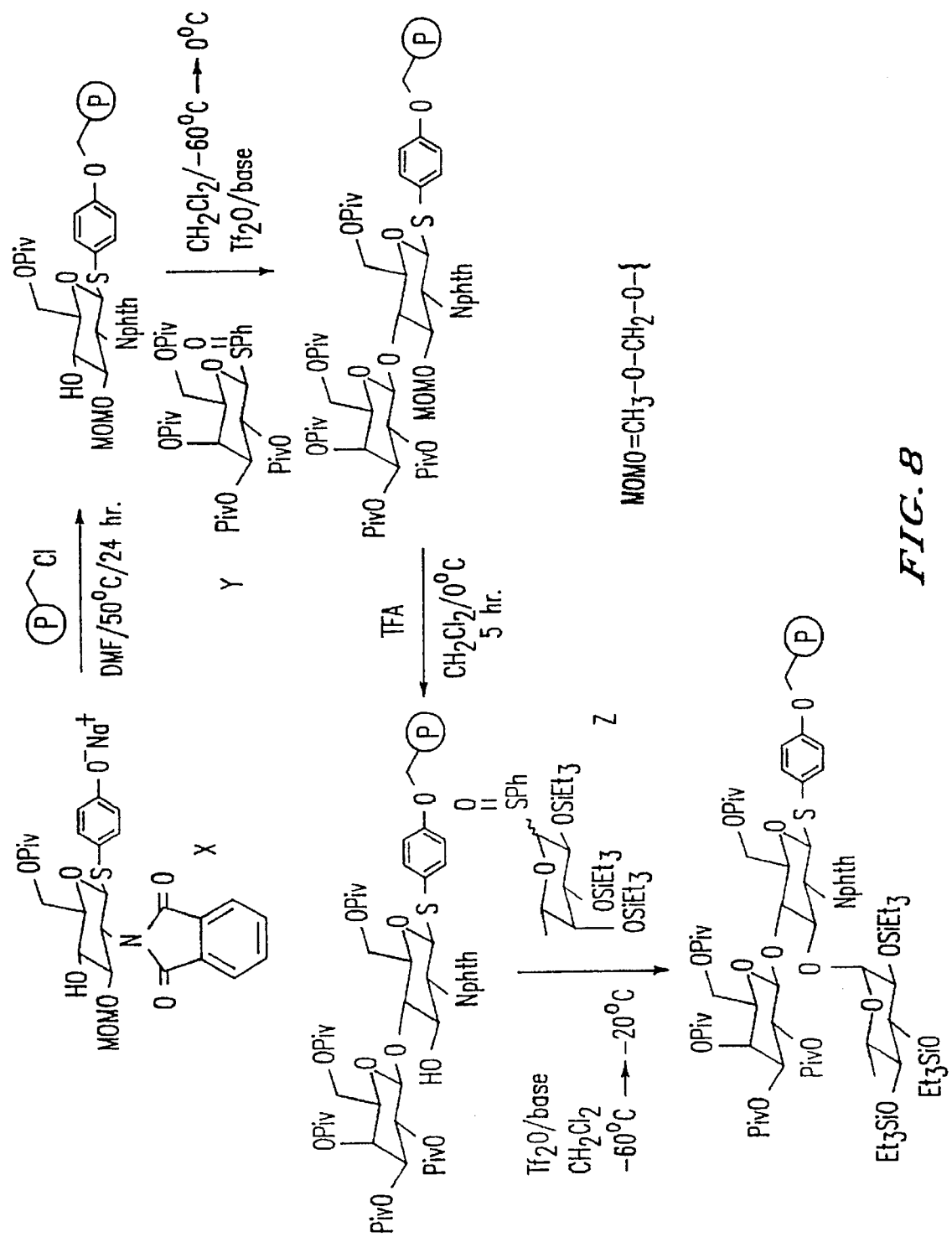
FIG. 8 illustrates the general scheme for synthesis of a trisaccharide on the solid phase.

Thiosugar X in FIG. 8, is prepared from the readily available glucosamine by treatment with (1) phthalic anhydride; (2) acetic anhydride; (3) tetrachlorotin-4-hydroxy thiophenol; (4) benzyl bromide; (5) hydroxide; (6) benzaldehyde-$H^+$; (7) chloromethyl methyl ether (MOM chloride); (8) $H_2O/H^+$; (9) pivalyoyl chloride; (10) hydrogenation, Pd(OH)$_2$; (11) NaH. Again, all steps are standard including the conditions for the deprotection of the benzyl protecting group on the 4-hydroxy thiophenyl glycoside, which conditions are typical for debenzylation. In the debenzylation step, no cleavage of the sugar to sulfur bond is observed.

Sulfoxide Y in FIG. 8 is prepared by treating perpivaloylated galactose with $BF_3$/etheratethiophenol, followed by mCPBA.

Sulfoxide Z in FIG. 8 is prepared by treating peracetylated fucose with $BF_3$/etheratethiophenol, followed sequentially by hydroxide, triethylsilyl chloride, and mCPBA.

STANDARD REFERENCES

Most of the transformations mentioned above (protection: benzylation, benzylidenation, acetonation, esterification, and carbo- or silylethentication of sugars; deprotection: debenzylation, acidic hydrolysis of benzylidenes or acetonates, basic hydrolysis of esters, removal of silyl groups with fluoride or under acidic conditions) are described in Binkley, R. W. *Modern Carbohydrate Chemistry*, Marcel Dekker, Inc.: New York, 1988. Methods to convert lactols or anomeric esters or anomeric esters to thiophenyl groups (to produce thiophenyl glycosides) are well known. See, e.g.: (a) Ferrier, R. J.; Hay, R. W.; Vethaviyasar, N., *Carbohydr. Res.* 1973, 27, 55. (b) Mukaiyama, T.; Nakatsuka, T.; Shoda, S. *Chem. Lett.* 1979, 487. (c) Van Cleve, J. W. *Carbohydr. Res.* 1979, 70, 161. (d) Hanessian, S.; Bacquet, D.; Lehong, N. *Carbohydr. Res.* 1980, 80, C17. (e) Garegg, P. J.; Henrichson, C.; Norberg, T. *Carbohydr. Res.* 1983, 116, 162. (f) Nicolaou, K. D.; Seitz, S. P.; Papahatjis, D. P. *J. Am. Chem. Soc.* 1983, 105, 2430.

What is claimed is:

1. A method of forming a glycosidic linkage on a solid phase comprising:
    (a) exposing, in an organic solvent, a glycosyl acceptor (GA) bound to a solid support to a glycoside (G) having an activated anomeric sulfoxide group, said GA having glycosyl accepting characteristics and said G having glycosyl donating characteristics; and
    (b) allowing a glycosylation reaction to proceed such that a glycosidic bond is formed which links said GA to the anomeric carbon of said G.

2. The method of claim 1 in which said GA is the sodium salt of the glycosyl acceptor of the formula X,

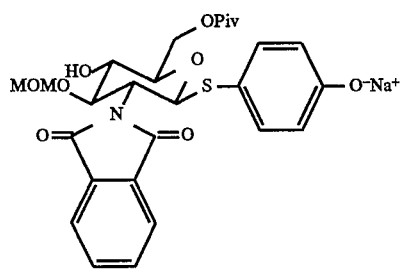

said solid support is a Merrifield resin, and said G is a 2,3,4,6-pivaloylated galactosyl sulfoxide of the formula Y

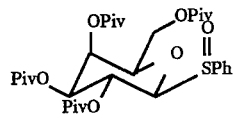

3. The method of claim 1 in which the glycosidic linkage formed is a 1,2-trans glycosidic linkage.

4. The method of claim 3 in which the glycoside (G) has a neighboring participating group (NPG) at the C-2 position.

5. The method of claim 4 in which said NPG is a pivaloyl group.

6. The method of claim 1 which is carried out in the presence of an effective amount of an acid scavenger or a sulfonic acid scavenger.

7. The method of claim 1 in which said G possesses a nucleophilic group blocked by a temporal protecting group (TPG).

8. The method of claim 7 which further comprises removing said TPG to uncover the nucleophilic group of said G.

9. The method of claim 8 which further comprises exposing the unblocked nucleophilic group of said G to a second glycoside (2G) having an activated anomeric sulfoxide group to form a glycosidic bond, which links said G to the anomeric carbon of said 2G, and to provide an oligosaccharide or glycoconjugate that is bound to the solid support having a sequence GA-G-2G.

10. The method of claim 9 in which said 2G possesses a nucleophilic group blocked by a TPG and which further comprises removing said TPG to uncover the nucleophilic group of said 2G.

11. The method of claim 10 which further comprises exposing said unblocked nucleophilic group of 2G to a third glycoside (3G) having an activated anomeric sulfoxide group to provide an oligosaccharide or glycoconjugate that is bound to the solid support having a sequence of GA-G-2G-3G.

12. The method of claim 11 in which subsequent glycosides are introduced to the growing oligosaccharide or glycoconjugate chain.

13. The method of claim 12 which further comprises intermediate washing steps.

14. The method of claim 1 in which the anomeric sulfoxide of glycoside (G) is activated by treatment with an effective amount of an activating agent.

15. The method of claim 14 in which said activating agent comprises triflic anhydride.

16. The method of claim 14 in which said activating agent comprises triflic acid.

17. The method of claim 1 in which said solid support comprises a polystyrene resin.

18. The method of claim 17 in which said polystyrene resin is a Merrifield resin.

19. The method of claim 17 in which said polystyrene resin is a PEG-derivatized polystyrene resin.

20. The method of claim 17 in which said polystyrene resin is a TentaGel™ resin.

* * * * *

UNITED STATES PATENT AND TRADEMARK OFFICE
CERTIFICATE OF CORRECTION

PATENT NO. : 5,639,866
DATED : June 17, 1997
INVENTOR(S) : Daniel E. Kahne

It is certified that error appears in the above-identified patent and that said Letters Patent is hereby corrected as shown below:

Title page, "20 claims" should read -- 19 claims--.

Claim 6, line 3, the "sulfonic" should be "sulfenic".

Signed and Sealed this

Sixteenth Day of December, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,639,866
DATED : June 17, 1997
INVENTOR(S) : Daniel E. Kahne

It is certified that error appears in the above-identified patent and that said Letters Patent is hereby corrected as shown below:

Col. 1, line 4, insert under "Title of invention" the following statement:

--Aspects of the present invention were supported by HHS R01 GM42733, HHS/NRSA F32 GM15051, and ONRN0014-91-J-1230. The United States Government has certain rights in the invention.--

Signed and Sealed this

First Day of June, 1999

Attest:

Q. TODD DICKINSON

*Attesting Officer*   *Acting Commissioner of Patents and Trademarks*